(12) United States Patent
Manning et al.

(10) Patent No.: US 10,967,040 B2
(45) Date of Patent: Apr. 6, 2021

(54) METHODS OF TREATING PRADER-WILLI SYNDROME WITH CARBETOCIN

(71) Applicant: Levo Therapeutics, Inc., Skokie, IL (US)

(72) Inventors: Mark C. Manning, Johnstown, CO (US); Ryan E. Holcomb, Fort Collins, CO (US); Derrick S. Katayama, Timnath, CO (US); Christopher Bryant, Burr Ridge, IL (US); Sara Cotter, Wilmette, IL (US); Joseph William Cormier, Bethesda, MD (US)

(73) Assignee: Levo Therapeutics, Inc., Skokie, IL (US)

(*) Notice: Subject to any disclaimer, the term of this patent is extended or adjusted under 35 U.S.C. 154(b) by 0 days.

(21) Appl. No.: 16/938,257

(22) Filed: Jul. 24, 2020

(65) Prior Publication Data

US 2020/0353029 A1 Nov. 12, 2020

Related U.S. Application Data

(63) Continuation of application No. 16/576,940, filed on Sep. 20, 2019.

(60) Provisional application No. 62/876,857, filed on Jul. 22, 2019, provisional application No. 62/734,152, filed on Sep. 20, 2018.

(51) Int. Cl.
| | | |
|---|---|---|
| *A61K 38/12* | (2006.01) | |
| *C07K 7/64* | (2006.01) | |
| *A61K 38/095* | (2019.01) | |
| *A61K 47/38* | (2006.01) | |
| *A61K 47/55* | (2017.01) | |
| *A61K 9/00* | (2006.01) | |
| *A61K 9/08* | (2006.01) | |

(52) U.S. Cl.
CPC .......... *A61K 38/095* (2019.01); *A61K 9/0043* (2013.01); *A61K 9/08* (2013.01); *A61K 47/38* (2013.01); *A61K 47/551* (2017.08)

(58) Field of Classification Search
None
See application file for complete search history.

(56) References Cited

U.S. PATENT DOCUMENTS

| | | | |
|---|---|---|---|
| 5,482,931 A | 1/1996 | Harris et al. | |
| 6,894,026 B1 | 5/2005 | Quay | |
| 7,879,976 B2 | 2/2011 | Friess et al. | |
| 8,263,125 B2 | 9/2012 | Vaya et al. | |
| 8,853,158 B2 | 10/2014 | Muscatelli et al. | |
| 8,865,746 B2 | 10/2014 | Vath | |
| 9,016,221 B2 | 4/2015 | Brennan et al. | |
| 9,023,793 B2 | 5/2015 | Leonard et al. | |
| 9,125,862 B2 | 9/2015 | Muscatelli et al. | |
| 9,566,311 B2 | 2/2017 | Siekmann et al. | |
| 9,605,051 B2 | 3/2017 | Soane et al. | |
| 9,751,870 B2 | 9/2017 | Bissantz et al. | |
| 9,789,155 B2 | 10/2017 | Young et al. | |
| 9,867,881 B2 | 6/2018 | Soane et al. | |
| 10,016,513 B2 | 7/2018 | Soane et al. | |
| 10,441,627 B2 | 10/2019 | Danglas et al. | |
| 10,842,775 B2 | 11/2020 | Burnett et al. | |
| 2004/0235956 A1 | 11/2004 | Quay | |
| 2007/0032410 A1 | 2/2007 | Quay et al. | |
| 2010/0158995 A1 | 6/2010 | Millan et al. | |
| 2010/0292437 A1 | 11/2010 | Nelson et al. | |
| 2010/0311655 A1 | 12/2010 | Leonard et al. | |
| 2012/0108510 A1 | 5/2012 | Young et al. | |
| 2012/0172304 A1* | 7/2012 | Leonard .................... | A61P 5/10 514/11.6 |
| 2013/0102528 A1 | 3/2013 | Muscatelli et al. | |
| 2013/0116215 A1 | 5/2013 | Coma et al. | |
| 2013/0210746 A1* | 8/2013 | Siekmann ............... | A61K 47/20 514/21.1 |
| 2014/0329747 A1 | 11/2014 | Tidmarsh | |
| 2015/0165139 A1 | 6/2015 | Hafner | |
| 2015/0216835 A1 | 8/2015 | Vath | |
| 2015/0284434 A1 | 10/2015 | Bissantz et al. | |
| 2016/0022726 A1 | 1/2016 | Feller et al. | |
| 2017/0056364 A1 | 3/2017 | Vath | |
| 2017/0081368 A1 | 3/2017 | Bissantz et al. | |
| 2017/0081369 A1 | 3/2017 | Bissantz et al. | |
| 2017/0106044 A1 | 4/2017 | Nilsson et al. | |

(Continued)

FOREIGN PATENT DOCUMENTS

| | | |
|---|---|---|
| CN | 102144965 A | 8/2011 |
| CN | 102977192 A | 3/2013 |

(Continued)

OTHER PUBLICATIONS

Avanti et al., "A new strategy to stabilize oxytocin in aqueous solutions: II. Suppression of cysteine-mediated intermolecular reactions by a combination of divalent metal ions and citrate," *Mol Pharm.*, 2012 9(3):554-62.

Avanti et al., "A new strategy to stabilize oxytocin in aqueous solutions: I. The effects of divalent metal ions and citrate buffer," *AAPSJ.* 2011, 13(2):284-290.

Avanti et al., "The Formation of Oxytocin Dimers is Suppressed by the Zinc-Aspartate-Oxytocin Complex," *Journal of Pharmaceutical Sciences*, (2013) vol. 102, 1734-1741.

(Continued)

*Primary Examiner* — Kevin S Orwig

(74) *Attorney, Agent, or Firm* — Cooley LLP

(57) ABSTRACT

The application describes stable aqueous compositions comprising relatively high concentrations of carbetocin and a solubilizer and/or surface active agent. The disclosed carbetocin compositions are effective in the treatment of a neurodevelopmental disorder, such as Präder-Willi syndrome. Additionally, the disclosed carbetocin compositions show improved stability at room temperature and/or under accelerated conditions of stress.

19 Claims, 6 Drawing Sheets

(56) References Cited

U.S. PATENT DOCUMENTS

| | | |
|---|---|---|
| 2017/0174725 A1 | 6/2017 | Bleicher et al. |
| 2017/0232059 A1 | 8/2017 | Uvnas-Moberg |
| 2017/0252546 A1 | 9/2017 | Park et al. |
| 2017/0304445 A1 | 10/2017 | Ogez et al. |
| 2017/0326200 A1 | 11/2017 | Danglas et al. |

FOREIGN PATENT DOCUMENTS

| | | | |
|---|---|---|---|
| WO | WO 95/25534 | 9/1995 | |
| WO | WO 2004/003145 | 1/2004 | |
| WO | WO 2007/141541 | 12/2007 | |
| WO | WO 2008/042452 | 4/2008 | |
| WO | WO 2008/150305 | 12/2008 | |
| WO | WO 2009/033782 | 3/2009 | |
| WO | WO 2009/033783 | 3/2009 | |
| WO | WO 2009/033820 | 3/2009 | |
| WO | WO 2009/043457 | 4/2009 | |
| WO | WO 2009/122285 | 10/2009 | |
| WO | WO 2011/035330 | 3/2011 | |
| WO | WO 2012/149472 | 3/2011 | |
| WO | WO 2011/147889 | 12/2011 | |
| WO | WO 2012/042371 | 4/2012 | |
| WO | WO 2014/107231 | 4/2014 | |
| WO | WO 2014/095773 | 6/2014 | |
| WO | WO 2014/111356 | 7/2014 | |
| WO | WO 2015/185467 | * 12/2015 | ............ A61K 38/08 |
| WO | WO 2015/185584 | 12/2015 | |
| WO | WO 2016/020349 | 2/2016 | |
| WO | WO 2016/044131 | * 3/2016 | ............ A61K 38/11 |
| WO | WO 2016/053091 | 4/2016 | |
| WO | WO 2016/077629 | * 5/2016 | ............... A61K 9/22 |
| WO | WO 2018/158234 | * 3/2017 | ............... A61K 9/00 |
| WO | WO 2017/210540 | * 6/2017 | ........... A61K 31/221 |
| WO | WO 2017/127287 | 7/2017 | |
| WO | WO 2018/158234 | 7/2018 | |

OTHER PUBLICATIONS

*Cromwell et al., "Protein Aggregation and Bioprocessing," *AAPS J.*, 2006;8(3):E572-E579.

Drew et al., "Size estimation of chemical space: how big is it?" *J. Pharm. Pharmacol.*, 2012; 64(4):490-5.

Frokjaer et al., "Protein drug stability: a formulation challenge," *Nat Rev Drug Discov.*, 2005; 4(4):298-306.

Gard et al., "Oxytocin preparation stability in several common obstetric intravenous solutions," *Am J Obstet Gynecol.*, 2002, 186(3):496-498.

Hawe et al., "Towards heat-stable oxytocin formulations: analysis of degradation kinetics and identification of degradation products," *Pharm Res.*, 2009, 26(7):1679-88.

Høgstedt et al., "Manipulating Aggregation Behavior of the Uncharged Peptide Carbetocin," *J. Pharm. Sci.*, 2018, 107(3):838-847.

Kiese et al., "Shaken, Not Stirred: Mechanical Stress Testing of an IgG1 Antibody," *J. Pharm. Sci.*, 2008, 97(10):4347-66.

Nucci et al., "Carbetocin for prevention of postcesarean hemorrhage in women with severe preeclampsia; a before-after cohort comparison with oxytocin," *J. Clin. Anesth.*, 2016, 35:321-325.

Pathak K., "Mucoadhesion; A prerequisite or a constraint in nasal drug delivery?" *Int J Pharm Investig.*, 2011, 1(2):62-3.

Payne R. W. et al., "Second virial coefficient determination of a therapeutic peptide by self-interaction chromatography," *Biopolymers*, 2006, 84:527-533.

Shire et al., "Challenges in the development of high protein concentration formulations," *J Pharm Sci.*, 2004, 93:1390-1402.

Teng et al., "Comparison of effectiveness and safety of carbetocin and oxytocin for prevention of postpartum hemorrhage after cesarean section," *Shengzhi Yixue Zazhi*, 2007, 16(2), 73-76.

Teng et al., "Study of drug control over postoperative hemorrhage after selective caesarean section," *J. Reprod. Med.*, 2006, vol. 15, 48-52.

Unterrainer et al., "Caesarean section and brain tumour resection," *Br J. Anaesth.*, Jul. 2011;107(1):111-2.

Widmer et al., "Room temperature stable carbetocin for the prevention of postpartum haemorrhage during the third stage of labour in women delivering vaginally: study protocol for a randomized controlled trial." *Trials*, 2016 17:143.

DaSilva, et al., "Investigations on the mechanism of aqueous solubility increase caused by some hydrotropes," *Thermochimica Acta* 328 (1999) 161-167.

Fabio, et al., "Heat-Stable Dry Powder Oxytocin Formulations for Delivery by Oral Inhalation," *AAPS PharmSciTech*, vol. 16, No. 6, Dec. 2015, 1299-1306.

Kumar et al., "Nasal-nanotechnology: revolution for efficient therapeutics delivery," (2016), *Drug Delivery*, 23:3, 671-683.

Li et al., Non-ionic surfactants as novel intranasal absorption enhancers: in vitro and in vivo characterization, *Drug Delivery*, (2016), 23:7, 2272-2279.

Madan et al., "Solubility enhancement studies on lurasidone hydrochloride using mixed hydrotropy," *International Journal of Pharmaceutical Investigation*, Apr. 2015, vol. 5, Issue 2, 114-120.

Marttin et al., "Efficacy, Safety and Mechanism of Cyclodextrins as Absorption Enhancers in Nasal Delivery of Peptide and Protein Drugs," *Journal of Drug Targeting*, 6:1, 17-36 (1998).

Murtaza et al., "Comparative evaluation of various solubility enhancement strategies for furosemide," *Pak. J. Pharm. Sci.*, vol. 27, No. 4, Jul. 2014, pp. 963-973.

Poole et al., "Formation of Amide- and Imide-Linked Degradation Products Between the Peptide Drug Oxytocin and Citrate in Citrate-Buffered Formulations," *Journal of Pharmaceutical Sciences*, vol. 100, No. 7, Jul. 2011.

Schreier et al., "Surface active drugs: self-association and interaction with membranes and surfactants. Physicochemical and biological aspects," *Biochimica et Biophysica Acta* 1508 (2000) 210-234.

Shimizu et al., "Hydrotropy: Monomer-Micelle Equilibrium and Minimum Hydrotrope Concentration," *J. Phys. Chem.* B 2014, 118, 10515-10524.

Williams et al., "In vitro and preclinical assessment of an intranasal spray formulation of parathyroid hormone PTH 1-34 for the treatment of osteoporosis," *International Journal of Pharmaceutics* 535 (2018) 113-119.

Panganiban et al., "Random heteropolymers preserve protein function in foreign environments," *Science* 359, 1239-1243 (2018).

Härtl, Elisabeth Barbara, "Novel Approaches for Stabilization and Characterization of Therapeutic Proteins in Liquid Formulations," Dissertation, Sep. 16, 2013, München, Germany.

"Current Solubilization Techniques: Insights from the BASF Solubilization Symposium," Feb. 2018.

Ku, Sherry, "Solutol HS15 as a Novel Excipient," *Pharmaceutical Technology*, vol. 34, Issue 11, 108-110.

Kaal, Andreas et al., "Occurrence and effects of octreotide antibodies during nasal, subcutaneous and slow release intramuscular treatment," *European Journal of Endocrinology* (2000) 143 353-361.

Roberts, Christopher J., "Therapeutic Protein Aggregation: Mechanisms, Design, and Control," *Trends Biotechnol.* Jul. 2014; 32(7): 372-380.

Hung, Nguyen Ba, "Sequence dependent aggregation of peptides and fibril formation," J. Chem. Phys. 147, 2017, 105102-1 to 105102-10.

Booth et al., "Hydrotrope accumulation around the drug: the driving force for solubilization and minimum hydrotrope concentration for nicotinamide and urea," *Phys. Chem. Chem. Phys.*, 2015, 17, 8028-8037.

Kim et al., "Hydrotropic Solubilization of Poorly Water-Soluble Drugs," Journal of Pharmaceutical Sciences, vol. 99, No. 9, Sep. 2010, 3953-3965.

Damiati et al., "Application of machine learning in prediction of hydrotrope-enhanced solubilisation of indomethacin", *International Journal of Pharmaceutics* 530 (2017) 99-106.

Dhapte et al., "Advances in hydrotropic solutions: An updated review," St. Petersburg Polytechnical University Journal: Physics and Mathematics 1 (2015) 424-435.

(56) References Cited

OTHER PUBLICATIONS

Dykens et al., "Intranasal carbetocin reduces hyperphagia in individuals with Prader-Willi syndrome," *JCI Insight*. 2018;3(12):e98333, 1-11.

Mitesh et al., "Formulation of carbetocin injection by lyophilization technique," Der Pharmacia Lettre, 2013 5(5): 200-205.

Baheti et al., "Excipients used in lyophilization of small molecules," *J. Excipients and Food Chem.* 1(1) 2010, 42-54.

Warnken et al., "Formulation and device design to increase nose to brain drug delivery," *Journal of Drug Delivery Science and Technology* 35 (2016) 213-222.

Casettari, et al., "Chitosan in nasal delivery systems for therapeutic drugs," *Journal of Controlled Release* 190 (2014) 189-200.

Quintana et al., "Evidence for intranasal oxytocin delivery to the brain: recent advances and future perspectives," *Ther. Deliv.* (2018) 9(7), 515-525.

Dua, R., "The Influence of Formulation and Device Variables on the Intranasal Absorption of Salmon Calcitonin," Open Access Dissertations, Paper 181, http://digtalcommonsuri.edu/oa_diss/181, (1995), 1-214.

Ayoub, Marwa, "Effect of some intranasal formulations used in the management of allergic rhinitis on mucociliary function," Thesis, University of Brighton, May 2015, 1-320.

Trows, et al., "Analytical Challenges and Regulatory Requirements for Nasal Drug Products in Europe and the U.S.," *Pharmaceutics* 2014, 6, 195-219.

Pu et al., "A Comparison of the Deposition Patterns of Different Nasal Spray Formulations Using a Nasal Cast," *Aerosol Science and Technology*, 48:930-938, 2014.

Merkus, P., "Current aspects of nasal drug delivery," Dissertation, (2006), 1-181.

Djupesland P.G., "Nasal drug delivery devices: characteristics and performance in a clinical perspective—a review," *Drug Deliv. and Transl. Res.* (2013) 3:42-62.

Moharil et al., "Nasal Dosage Forms and Devices for Intranasal Drug Delivery," *World Journal of Pharmacy and Pharmaceutical Sciences*, vol. 3, Issue 4, 554-571.

Meredith et al., "Intranasal Delivery of Proteins and Peptides in the Treatment of Neurodegenerative Diseases," *The AAPS Journal*, vol. 17, No. 4, Jul. 2015, 780-787.

Shah et al., "Nasal Delivery of Proteins and Peptides," *Glob J Pharmaceu Sci*, vol. 1, Issue 4, Apr. 2017, 1-3.

Ghori et al., "Nasal Drug Delivery Systems: An Overview," *American Journal of Pharmacological Sciences*, 2015, vol. 3, No. 5, 110-119.

Yarragudi, S.B., "Formulation Strategies to Enhance Nose-to-Brain Delivery of Drugs," Thesis, University of Otago Duedin, New Zealand, Jun. 2018, 1-256.

Elder, D.P., "Antimicrobial Preservatives Part Two: Choosing a Preservative," *American Pharmaceutical Review*, Jan. 1, 2012 1-8.

Hofmann et al., "Influence of Preservatives and Topical Steroids on Ciliary Beat Frequency in Vitro," *Arch Otolaryngol Head Neck Surg*, vol. 130, Apr. 2004, 130:440-445.

Cho et al., "Long-Term Use of Preservatives on Rat Nasal Respiratory Mucosa: Effects of Benzalkonium Chloride and Potassium Sorbate," *Laryngoscope* (2000) 110:312-317.

Whitaker et al., "A Formulation Development Approach to Identify and Select Stable Ultra-High-Concentration Monoclonal Antibody Formulations With Reduced Viscosities," *J. Pharm. Sci.*, 106 (2017) 3230-3241.

Mathaes et al., "Application of different analytical methods for the characterization of non-spherical micro-and nanoparticles," *International Journal of Pharmaceutics*, 453 (2013) 620-629.

Maddux et al., "Microflow Imaging Analyses Reflect Mechanisms of Aggregate Formation: Comparing Protein Particle Data Sets Using the Kullback-Leibler Divergence," *J. Pharm. Sci.*, 106 (2017) 1239-1248.

Koepf et al., "Notorious but not understood: How liquid-air interfacial stress triggers protein aggregation," *International Journal of Pharmaceutics*, 537 (2018) 202-212.

Hofmann et al., "Predictive Screening Tools Used in High-Concentration Protein Formulation Development," *J. Pharm. Sci.*, 107 (2018) 772-777.

Kheddo et al., "The effect of arginine glutamate on the stability of monoclonal antibodies in solution," *International Journal of Pharmaceutics*, 473 (2014) 126-133.

Høgstedt, U.B., "Formulation of concentrated peptide solutions—physical stability challenges and the impact on peptide-peptide interactions," Industrial PhD Thesis, submitted to the Graduate School of the Faculty of Health and Medicinal Sciences, University of Copenhagen. Copenhagen, Nov. 2017.

Hodgdon, T.K. and Kaler, E.W., "Hydrotropic solutions," *Curr. Opin. in Colloid & Interface Sci.* 2007;12(3):121-128.

International Search Report for International Application No. PCT/US19/52092, dated Nov. 20, 2019.

Written Opinion of the International Search Authority for International Application No. PCT/US19/52092, dated Nov. 20, 2019.

Holland, A., "Understanding the eating disorder affecting people with Prader-Willi syndrome," *Journal of Applied Research in Intellectual Disabilities*, 1998, 11(3):192-206.

Goldstone, A.P. "Prader-Willi syndrome: advances in genetics, pathophysiology and treatment," *Trends in Endocrinology and Metabolism*, Jan. 2004-Feb. 2004, 15(1):12-20.

Eiholzer and Whitman, "A Comprehensive Team Approach to the Management of Patients with Prader-Willi Syndrome," Journal of Pediatric Endocrinology and Metabolism, Sep. 2004, 17(9):1153-1175.

Swaab, "Neuropeptides in Hypothalamic Neuronal Disorders," Jeon, KW [Editor]. *Int. Rev. Cytol.*, 2004, pp. 305-375.

Manning et al., "Peptide and non-peptide agonists and antagonists for the vasopressin and oxytocin V1a, V1b, V2 and OT receptors: research tools and potential therapeutic agents," *Prog Brain Res*, 2008, 170:473-512.

Marazziti et al., "The Role of Oxytocin in Neuropsychiatric Disorders," *Current Medicinal Chemistry*, 2008, 15(7):698-704.

"Comparative Study Between Prader-Willi Patients Who Take Oxytocin Versus Placebo," NCT01038570 clinicaltrials.gov, University Hospital, Toulouse, Dec. 23, 2009.

Schaller, "A single postnatal injection of oxytocin rescues the lethal feeding behaviour in mouse newborns deficient for the imprinted Magel2 gene," *Human Molecular Genetics*, Dec. 15, 2010, 19(24):4895-905.

Olszewski et al., "Oxytocin as Feeding Inhibitor: Maintaining Homeostasis in Consummatory Behavior," *Pharmacology Biochemistry and Behavior*, Nov. 2010, 97(1):47-54.

Mcallister, "Development of the eating behaviour in Prader-Willi Syndrome: advances in our understanding," *International Journal of Obesity*, Feb. 2011, 35(2):188-97.

Smith et al., "Prader-Willis Syndrome [PWS]—Is Behavioral Modification Possible?", (abstract), *Twin Research and Human Genetics*, Aug. 2011, 14(4):350-351.

Tauber, et al., "Oxytocin may be useful to increase trust in others and decrease disruptive behaviours in patients with Prader-Willi syndrome: a randomised placebo-controlled trial in 24 patients," *Orphanet Journal of Rare Diseases*, Jun. 24, 2011, 6:47.

VerticalNews.com, "Prader-Willi Syndrome; Oxytocin promises hope in Prader-Willi syndrome," *NewsRx Health & Science* [Atlanta], Jul. 17, 2011, 194.

Striepens et al., "Prosocial effects of oxytocin and clinical evidence for its therapeutic potential," *Frontiers in Neuroendocrinology*, Oct. 2011, 32(4):426-450.

Deblon, "Mechanisms of the Anti-Obesity Effects of Oxytocin in Diet-Induced Obese Rats," PLoS ONE, Sep. 27, 2011, 6(9):e25565.

Kelly and Feifel, "Emerging Clinical Evidence on Oxytocin in Schizophrenia," (abstract), *Schizophrenia Research*, Apr. 2012, 136(Supp. 1):S69.

Onaka, Jichi, "Roles of Oxytocin Neurones in the Control of Stress, Energy Metabolism, and Social Behaviour," *Journal of Endocrinology*, Apr. 2012, 24:587-598.

Goldstone, "Appetite hormones and the transition to hyperphagia in children with Prader-Willi syndrome," *International Journal of Obesity*, Dec. 2012, 36(12):1564-1570.

(56) References Cited

OTHER PUBLICATIONS

"Tolerance of Intranasal Administration of OT in Prader-Willi Newborn Babies," NCT01548521 clinicaltrials.gov, University Hospital, Toulouse, Mar. 8, 2012.

"Public summary of opinion on orphan designation. Carbetocin for the treatment of Prader-Willi syndrome," Public summary of opinion on orphan designation EMA/COMP/69949/2012.

Chapman et al., "Intranasal Treatment of Central Nervous System Dysfunction in Humans," *Pharmaceutical Research*, Oct. 2013, 30(10):2475-2484.

Ho, "Coming Full Circle: Contributions of Central and Peripheral Oxytocin Actions to Energy Balance," *Endocrinology*, Feb. 2013, 154(2):589-596.

De Berardis, G., "The Role of Intranasal Oxytocin in the Treatment of Patients with Schizophrenia: A Systematic Review," *CNS & Neurological Disorders-Drug Targets*, Mar. 2013, 12(2):252-264.

Bakermans-Kranenburg and van IJzendoorn, "Sniffing around oxytocin: review and meta-analyses of trials in healthy and clinical groups with implications for pharmacotherapy," *Translational Psychiatry*, 2013, 3:1-14.

Harris, "Therapeutic Interventions With Oxytocin: Current Status and Concerns," *Journal of the American Academy of Child & Adolescent Psychiatry*, Oct. 2013, 52(10):998-1000.

Ott et al., "Oxytocin Reduces Reward-Driven Food Intake in Humans," *Diabetes*, Oct. 2013, 62(10):3418-3425.

NewsRx, "Chu De Toulouse; Agency Reviews Patent Application Approval Request for Methods and Pharmaceutical Composition for the Treatment of a Feeding Disorder with Early-Onset in a Patient," *Genetics & Environmental Law Weekly* [Atlanta], May 18 2013):225.

"Oxytocin Trial in Prader-Willi Syndrome," NCT02013258 clinicaltrials. gov, University of Florida, Dec. 17, 2013.

Heymsfield, "Hyperphagia: Current Concepts and Future Directions Proceedings of the 2nd International Conference on Hyperphagia," *Obesity*, 2014, 22:S1-S17.

Bueno Diez, "Prader-Willi syndrome and hyperphagia: A challenge to investigate," *Endocrinol. Nutr.*, 2014, 61:121-122.

Pollack, "Seeking Clues to Obesity in Rare Hunger Disorder: [Business/Financial Desk]," *New York Times*, Late Edition (East Coast) [New York, N.Y] (Jan. 15, 2014): B.1.

Badiu and Marginean, "Current status and perspectives in the Treatment of Prader-Willi syndrome," *Expert Opinion on Orphan Drugs*, Apr. 2014, 2(4):337-347.

FDA, "Search orphan drug designations and approvals," https://www.accessdata.fda.gov /scripts/opdlisting/oopd/detailedIndex.cfm?cfgridkey=20144230. Last accessed: Jul. 12, 2020.

Einfeld SL et al., "A Double-Blind Randomized Controlled Trial of Oxytocin Nasal Spray in Prader Willi Syndrome," *American Journal of Medical Genetics*, Part A, Sep. 2014, 164A(9):2232-9.

Dutch Growth Research Foundation, "Intranasal administration of oxytocin in children and young adults with Prader-Willi Syndrome. A randomized, double-blind, placebo-controlled trial. Effects on satiety and food intake, and social behaviour," AdisInsight: Trials, Jul. 30, 2014.

"Evaluation of Tolerance, Suckling and Food Intake After Repeated Nasals Administrations of Oxytocin in PWS Infants," U.S. National Library of Medicine, ClinicalTrials.gov Identifier: NCT02205034, Last update May 12, 2017, https://clinicaltrials.gov/ct2/show/NCT02205034. Last accessed Jul. 11, 2020.

NewsRx, "Clinical Research; Findings in the Area of Clinical Trials and Studies Reported from University of Sydney (A Double-Blind Randomized Controlled Trial of Oxytocin Nasal Spray in Prader Willi Syndrome) (A Double-Blind Randomized Controlled Trial of Oxytocin Nasal)," *Biotech Week* [Atlanta] (Sep. 24, 2014): 481.

Terne, F., NMR Study on the Aggregation Behavior of the Therapeutic Peptide Carbetocin, *Master Thesis in Pharmaceutical Technology*, Lund University, 2018.

Zapadka K.L. et al. Factors affecting the physical stability (aggregation) of peptide therapeutics. *Interface Focus*, pp. 1-18, 2017;7(6).

International Search Report for International Application No. PCT/US19/52090, dated Nov. 21, 2019.

Written Opinion of the International Search Authority for International Application No. PCT/US19/52090, dated Nov. 21, 2019.

"NEW Tool to Help Measure Anxiety and Distress in PWS," https://www.fpwr.org/blog/new-tool-to-help-measure-anxiety-and-distress-in-pws, Jul. 20, 2018, 5 pages.

"Zafgen Donates Hyperphagia Questionnaire to FPWR for Use in Clinical Trials," https://www.fpwr.org/blog/zafgen-donates-hyperphagia-questionnaire-to-fpwr-for-use-in-clinical-trials, Nov. 30, 2016, 6 pages.

Busner et al., "The clinical global impressions scale: applying a research tool in clinical practice," Psychiatry (Edgmont) Jul. 2007;4(7):28-37.

Dykens et al., "Assessment of hyperphagia in Prader-Willi syndrome," Obesity (Silver Spring) Jul. 2007;15(7):1816-26.

Guy, "Clinical Global Impression (CGI)," ECDEU Assessment Manual for Psychopharmacology. 1976. Rockville, MD, U.S. Department of Health, Education, and Welfare, 2 pages.

McCandless et al., "Effects of MetAP2 inhibition on hyperphagia and body weight in Prader-Willi syndrome: a randomized, double-blind, placebo-controlled trial," Clinical Trial Diabetes Obes Metab . Dec. 2017;19(12):1751-1761.

Milner et al., "Prader-Willi syndrome: intellectual abilities and behavioural features by genetic subtype," J Child Psychol Psychiatry, Oct. 2005;46(10):1089-96.

Scahill et al., "Children's Yale-Brown Obsessive Compulsive Scale: reliability and validity," J Am Acad Child Adolesc Psychiatry, Jun. 1997;36(6):844-52.

\* cited by examiner

METHODS OF TREATING PRADER-WILLI SYNDROME WITH CARBETOCIN

DESCRIPTION OF THE DISCLOSURE

This application is a continuation of pending U.S. patent application Ser. No. 16/576,940, filed Sep. 20, 2019, which claims the benefit of priority from U.S. Provisional Patent Application No. 62/734,152, filed Sep. 20, 2018, and U.S. Provisional Patent Application No. 62/876,857, filed Jul. 22, 2019, all of which are incorporated herein by reference.

FIELD OF THE DISCLOSURE

The present disclosure relates to stable intranasal pharmaceutical preparations of carbetocin, including those that demonstrate improved stability under various long-term storage conditions and/or under accelerated conditions of stress. The present disclosure also relates to methods of preparing such pharmaceutical preparations. The present disclosure further relates to kits and the use of the intranasal pharmaceutical preparations for the treatment of neurodevelopmental disorders, such as Präder-Willi syndrome, and related symptoms.

BACKGROUND OF THE DISCLOSURE

Although both peptides and proteins are composed of amino acids, peptides are typically distinguished from proteins as having a shorter amino acid sequence, such as, for example, less than 50 amino acids. Because of this difference in size, peptides and proteins often possess different three-dimensional structures, properties, and functions. Peptides are used to treat various diseases and conditions. Owing to their low oral bioavailability, most peptides are administered parenterally. (Frokjaer S. et al. (2005) Nat Rev Drug Discov. 4:298-306.) Parental drug delivery includes intravenous, subcutaneous (s.c.), and intramuscular routes of administration. An alternative to parenteral injections is nasal drug administration. (Pathak K. (2011) Int J Pharm Investig. 1(2): 62-63.) Nasal drug delivery has several advantages, including systemic delivery that avoids first-pass metabolism, easy administration, rapid onset of effect, and the possibility to circumvent the blood-brain barrier. In addition, intranasal administration offers several practical advantages either from the viewpoint of patients (e.g., noninvasiveness, essentially painless, ease of drug delivery, and favorable tolerability profile) or pharmaceutical industry (e.g., sterilization of nasal preparations is often unnecessary).

Depending on potency, it may be necessary to formulate a peptide at a high concentration, but doing so may increase the likelihood of peptide aggregation. (Shire S. J. et al. (2004) J Pharm Sci. 93:1390-1402; Payne R. W. et al. (2006) Biopolymers 84:527-533.) One way to mitigate peptide aggregation is to formulate the peptide at a pH far from its isoelectric point to generate a high net charge. But for peptides without ionizable groups, pH optimization may not be possible. Consequently, maintaining a sufficient stability at high peptide concentrations may be challenging, especially since peptides generally do not possess higher-order structure, and their physical stability thus primarily depends on the nature of their peptide-peptide interactions. Peptides in solution may also degrade via, e.g., deamidation, oligomerization, and oxidation, making refrigeration in some cases necessary.

Carbetocin [(1-desamino-1-monocarba-2(O-methyl)-tyrosine) oxytocin] is an example of an uncharged peptide. Carbetocin is a long-acting synthetic oxytocin analog. The structure of carbetocin is shown below.

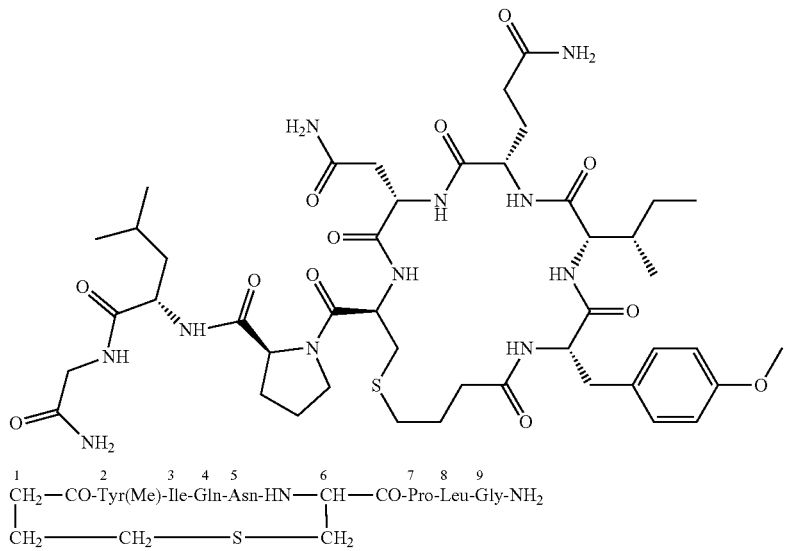

Carbetocin is an unusual peptide: it is small (8 amino acids); possesses no charge, is cyclic, and is highly lipophilic. It is also known that carbetocin lacks a stable and well-defined tertiary structure. Carbetocin is currently used outside the U.S. to treat or prevent postpartum hemorrhage during or following caesarean section. As such, carbetocin is administered by slow intravenous (IV) single injection at a dose of 100 µg. This formulation (Duratocin®, Ferring) requires refrigeration and contains 0.1 mg/mL of carbetocin, 9 mg sodium chloride, acetic acid—glacial to pH 3.8 and water for injection to 1 mL. (Widmer M. et al. (2016) Trials. 17:143.) Carbetocin (IV form) is currently registered in more than 70 countries under the trade names PABAL/DURATOCIN/LONACTENE/DURATOBAL.

Another injectable carbetocin drug product currently in clinical trials, CARBETOCIN RTS, can be stored at 30° C. for at least 3 years. (Widmer M. et al. (2016) Trials. 17:143.) Other prior attempts to develop a heat-stable oxytocin formulation for injection have been unsuccessful. (Hawe A. et al. (2009) Pharm Res. 26(7):1679-1688; Avanti C. et al. (2012) Mol Pharm. 9(3):554-562; Avanti C. et al. (2011) AAPSJ. 13(2):284-290; Gard J. W. et al. (2002) Am J Obstet Gynecol. 186(3):496-498.) This room temperature stable (RTS) variant of carbetocin has recently been developed and is now approved in the European Union; this variant differs from the current carbetocin formulation in its excipients. CARBETOCIN RTS contains 0.1 mg/mL of carbetocin, 1.19 succinic acid, 47.0 mg/mL mannitol, 1 mg/mL L-methionine, sodium hydroxide 2N to pH 5.45, and water for injection to 1 mL. (Widmer M. et al. (2016) Trials. 17:143.)

Other attempts have been made to make stable high carbetocin formulations using typical peptide excipients (e.g., surfactants); however, none of the studied excipients prevented carbetocin aggregation. (Hegstedt U. B. et al. (2018). J Pharm Sci. 107(3):838-847.) Only in the absence of headspace was 15 mM sodium dodecyl sulfate (SDS) capable of preventing shaking induced carbetocin aggregation.

In addition, when aqueous carbetocin solutions are manufactured, packaged, transported, stored, and handled prior to administration to a patient, they are subject to mechanical and chemical stresses. These types of stresses can be detrimental to various formulations of carbetocin in solution.

Given the propensity of carbetocin to aggregate in solution, a stable carbetocin pharmaceutical formulation that optimizes and extends carbetocin's in-use period, as well as delivers relatively high content uniformity is desirable. For example, an intranasal formulation that can be thawed by a patient and used for several days without aggregation or a change in the carbetocin content from one dose to another would enhance patient compliance and safety.

Thus, given carbetocin's strong propensity to aggregate in solution, there remains a need for stable carbetocin pharmaceutical preparations, including those that are stable to stress, that show relatively high content uniformity of carbetocin over long periods of time before and after one or more freeze/thaw cycles, are suitable for intranasal administration, provide enhanced convenience and patient compliance, and/or are highly concentrated.

SUMMARY OF THE DISCLOSURE

It has been surprisingly found that improved carbetocin pharmaceutical preparations can be prepared with certain solubilizers and/or surface active agents, such as a viscoelastic polymer, for example, hydroxypropyl methylcellulose (HPMC), including those that contain high concentrations of carbetocin and that are stable under conditions of stress.

For example, the pharmaceutical preparations of the present disclosure remain unexpectedly stable even at relatively high concentrations of carbetocin (e.g., greater than about 10 mg/mL to about 70 mg/mL) and under accelerated stress conditions. In some embodiments of the present disclosure, carbetocin is present in a pharmaceutical preparation in a concentration of at least 10 mg/mL, which is 100 times greater than that of the DURATOCIN® and CARBETOCIN RTS products referenced above. The carbetocin pharmaceutical preparations disclosed herein also exhibit improved stability even under conditions of mechanical stress and for extended periods of time. In addition, the pharmaceutical preparations of the present disclosure are suitable for intranasal administration.

In certain embodiments, the stable intranasal pharmaceutical preparation comprises an aqueous solution of carbetocin and a solubilizer and/or surface active agent. In at least one embodiment, the pharmaceutical preparation does not include a surfactant (e.g., n-dodecyl-β-D-maltoside (DDM), poloxamer 188, polysorbate 20 or polysorbate 80, sodium dodecyl sulfate). In at least one embodiment, the pharmaceutical preparation does not have reduced headspace, i.e., the container is not completely full.

In at least one embodiment, the present disclosure is directed to a stable intranasal pharmaceutical preparation comprising an aqueous solution of carbetocin and a solubilizer and/or surface active agent, wherein the solution has no visible solids after being subjected to agitation stress conditions. Such a preparation may be sufficiently stable even under conditions of stress (e.g., shaking and stirring, pumping, freeze-thaw processes) for extended periods of time with little to no visible solids. In at least some embodiments, the pharmaceutical preparation has little to no aggregates by visual assessment, including photographs.

In at least one embodiment, the present disclosure is directed to a stable intranasal pharmaceutical preparation comprising an aqueous solution of carbetocin and a solubilizer and/or surface active agent, such as HPMC, wherein the resulting preparation exhibits a relatively high content uniformity of carbetocin for long periods of time at room temperature, and also after one or more freeze/thaw cycles.

For example, the disclosed preparations show content uniformity of carbetocin after thawing for up to 7 days (longer shelf life and/or in-use period). In at least some embodiments, the disclosed carbetocin preparation is stable and does not aggregate for a period of time after one or more freeze/thaw cycles. In some embodiments, the pharmaceutical preparation has little to no aggregates by visual assessment, which may include photographs. In some embodiments, the carbetocin in the disclosed preparation is evenly distributed throughout the preparation to ensure that if the preparation is, for example, split in one or more preparations, each resulting preparation has an equal dose of carbetocin. In one embodiment, the disclosed carbetocin preparations have a consistent dose of carbetocin, which is maintained between various preparation batches so that the patient receives the correct dose consistently over various administrations. In at least one embodiment, the disclosed carbetocin preparations provide enhanced convenience and patient compliance.

In at least one embodiment, the concentration of carbetocin ranges from about 10 mg/mL to about 70 mg/mL. In at least one embodiment, the concentration of carbetocin ranges from about 10 mg/mL to about 40 mg/mL. In at least one embodiment, the concentration of carbetocin ranges from about 11 mg/mL to about 36 mg/mL. In at least one embodiment, the concentration of carbetocin is about 34.3 mg/mL. In at least one embodiment, the concentration of carbetocin is about 11.4 mg/mL. In some embodiments, the high concentration carbetocin pharmaceutical preparation has no visible solids when stored at room temperature (e.g., 25° C.) for a sustained period of time. For example, the carbetocin pharmaceutical preparation has no visible solids for up to 3 years. In some embodiments, the carbetocin pharmaceutical preparation has no visible solids for 2 years. In some embodiments, the carbetocin pharmaceutical preparation has no visible solids for 1 year. In some embodiments, the carbetocin pharmaceutical preparation has no visible solids for up to 3 years when the headspace is near zero. In one embodiment, the carbetocin pharmaceutical preparation has no visible solids for up to 3 years when the headspace is substantially zero.

In at least some embodiments, the pharmaceutical preparation of carbetocin comprises a hydrotrope and/or HPMC, and the concentration of carbetocin in the preparation ranges from about 1 mg/mL to about 15 mg/mL. In at least one embodiment, the concentration of carbetocin ranges from about 1 mg/mL to about 10 mg/mL. In at least one embodiment, the concentration of carbetocin ranges from about 1 mg/mL to about 5 mg/mL. In at least one embodiment, the concentration of carbetocin is about 1 mg/mL. In at least one embodiment, the concentration of carbetocin is about 11.4 mg/mL. In some embodiments, the carbetocin pharmaceutical preparation has no visible solids when stored at room temperature (e.g., 25° C.) for a sustained period of time. For example, the carbetocin pharmaceutical preparation has no visible solids for up to 3 years. In some embodiments, the carbetocin pharmaceutical preparation has no visible solids for up to 3 years when the headspace is near zero. In one embodiment, the carbetocin pharmaceutical preparation has no visible solids for up to 3 years when the headspace is substantially zero.

In some embodiments, the concentration of carbetocin in the pharmaceutical preparation does not change over time (e.g., storage at 40° C. for 1 week, 40° C. for 2 weeks, 40° C. for 3 weeks, 40° C. for 4 weeks, 40° C. for 5 weeks). In at least one embodiment, carbetocin is not subject to chemical degradation as measured by HPLC. For example, the chromatographic purity of carbetocin is greater than 98%. In at least one embodiment, the chromatographic purity of carbetocin is greater than 99%. In at least one embodiment, the chromatographic purity of carbetocin is greater than 99.4%. In at least one embodiment, the chromatographic purity of carbetocin is greater than 99.5%.

In at least one embodiment, the carbetocin pharmaceutical preparation is stable to shaking stress. In some embodiments, the preparation is subjected to shaking stress for at least 14 days when the headspace is limited, and the aqueous carbetocin solution remains clear with little to no visible particles. In some embodiments, the preparation is subjected to intermittent shaking stress for at least 14 days, and the aqueous carbetocin solution remains clear with little to no visible particles. In at least one embodiment, carbetocin does not chemically degrade before or after shaking stress. For example, the chromatographic purity of carbetocin is greater than 98%. In at least one embodiment, the chromatographic purity of carbetocin is greater than 99%. In at least one embodiment, the chromatographic purity of carbetocin is ≥99.4. In at least one embodiment, the chromatographic purity of carbetocin is ≥99.5. Such chromatographic purity occurs with and without exposure to shaking stress.

The pharmaceutical preparations of carbetocin disclosed comprise a solubilizer and/or HPMC. The solubilizer is chosen from an amino acid, an interfacial stabilizer, or a hydrotrope. In at least one embodiment, the amino acid may be chosen from a natural or unnatural amino acid. In one embodiment, the natural amino acid is arginine. In at least some embodiments, the unnatural amino acids may be chosen from β-amino acids, homo-amino acids, proline and pyruvic acid derivatives, 3-substituted alanine derivatives, glycine derivatives, ring-substituted phenylalanine and tyrosine derivatives, linear core amino acids, or N-methyl amino acids. In some embodiments, the unnatural amino acid is an arginine derivative chosen from L-2-amino-3-guanidinopropionic acid hydrochloride and 4-guanidinobutyric acid. In at least one embodiment, the interfacial stabilizer is a cyclodextrin derivative. In at least one embodiment, the cyclodextrin may be chosen from methyl-β-cyclodextrin, randomly methylated-β-cyclodextrin (RM-β-CD), sulfobutylether-β-cyclodextrin (SBE-β-CD), epichlorohydrin-β-cyclodextrin, and carboxy methyl epichlorohydrin beta cyclodextrin. In at least one embodiment, the cyclodextrin is methyl-β-cyclodextrin. In at least one embodiment, the hydrotrope is an aromatic anionic compound. In at least one embodiment, the hydrotrope is selected from the group consisting of nicotinamide, sodium benzoate, and salicylate salts (e.g., sodium salicylate, potassium salicylate, lithium salicylate, ammonium salicylate, calcium salicylate, and magnesium salicylate).

In at least one embodiment, the pharmaceutical preparation comprises nicotinamide. In another embodiment, the pharmaceutical preparation comprises sodium salicylate. In some embodiments, the pharmaceutical preparation comprises nicotinamide, sodium benzoate, salicylate salt (e.g., sodium salicylate), methyl-β-cyclodextrin, or arginine and HPMC. The pharmaceutical preparation of the present disclosure may also include additional excipients, such sorbitol, mannitol, glycine, lactose, trehalose, ethylenediaminetetraacetic acid (EDTA), potassium sorbate, acetate, and methyl-β-cyclodextrin among others. In at least one embodiment, the additional excipient is sorbitol.

If present in the pharmaceutical preparation, the solubilizer may be chosen from a cyclodextrin derivative. In at least some embodiments, the cyclodextrin derivative is chosen from methyl-β-cyclodextrin, randomly methylated-β-cyclodextrin (RM-β-CD), sulfobutylether-β-cyclodextrin (SBE-β-CD), epichlorohydrin-β-cyclodextrin, and carboxy methyl epichlorohydrin beta cyclodextrin. In some embodiments, the cyclodextrin derivative is methyl-β-cyclodextrin.

If present in the pharmaceutical preparation, the surface active agent may be chosen from a viscoelastic polymer, for example, hydroxypropyl methylcellulose (HPMC). In at least some embodiments, the surface active agent is a cellulose derivative. In at least one embodiment, the cellulose derivative may be chosen from hydroxypropyl cellulose (HPC), hydroxypropyl methylcellulose (HPMC), and carboxy methyl ethyl cellulose (CMEC). In some embodiments, the cellulose derivative is HPMC. If present in the pharmaceutical preparation, HPMC is present in an amount ranging from 0.005% to 0.05% w/v. In at least one embodiment, HPMC is present in an amount ranging from 0.0075% to 0.0125% w/v. And, in some embodiments, HPMC is present in an amount ranging from 0.0075% to 0.01% w/v. In at least one embodiment, HPMC is high viscosity grade. In at least one embodiment, the high viscosity HPMC is 4000 cP.

If present in the pharmaceutical preparation, nicotinamide is present in a concentration ranging from 50 mM to 500 mM. In at least one embodiment, the concentration of nicotinamide is about 400 mM. In at least one embodiment, the concentration of nicotinamide is about 300 mM. In another embodiment, the concentration of nicotinamide is about 200 mM.

If present in the pharmaceutical preparation, sodium salicylate is present in a concentration ranging from 50 mM to 500 mM. In at least one embodiment, the concentration of sodium salicylate is about 400 mM. In at least one embodiment, the concentration of sodium salicylate is about 300 mM. In another embodiment, the concentration of sodium salicylate is about 200 mM.

In some embodiments, the pharmaceutical preparation further comprises a tonicity enhancer to adjust the osmolality from about 220 mOsm/Kg to about 370 mOsm/Kg. In at least one embodiment, the osmolality is about 225 mOsm/Kg. In at least one embodiment, the osmolality is about 290 mOsm/Kg. In at least one embodiment, the osmolality is about 352 mOsm/Kg. In at least one embodiment, the osmolality is about 370 mOsm/Kg. In at least one embodiment, the tonicity enhancer is sorbitol. In some embodiments, sorbitol is present in a concentration ranging from 100 mM to 287 mM. In at least one embodiment, the concentration of sorbitol is about 110 mM. In at least one embodiment, the concentration of sorbitol is about 130 mM.

In at least one embodiment, the pH of the carbetocin pharmaceutical preparation ranges from 3.0 to 5.8, for example, from 3.5 to 5.75, from 5.15 to 5.65, from 5.25 to 5.55, or 5.35 to 5.45. In at least one embodiment, the pH is 5.4±0.5. In another embodiment, the pH is 5.4±0.3. In one embodiment, the pH is about 5.4±0.1.

The stable pharmaceutical preparation of the present disclosure may be formulated in a container. The container is chosen from an ampoule, vial, or pre-filled intranasal delivery device.

The present disclosure is also directed to a stable pharmaceutical preparation comprising an aqueous solution of carbetocin and a solubilizer and/or HPMC in a container, wherein the concentration of carbetocin ranges from about 1 mg/mL to about 70 mg/mL, and wherein the headspace in the container is near zero (i.e., limited headspace). In one embodiment, the headspace in the container is substantially zero.

In at least one embodiment, a stable intranasal pharmaceutical preparation comprises:
 (a) an aqueous solution of carbetocin, wherein the concentration of carbetocin ranges from about 10 mg/mL to about 70 mg/mL; and
 (b) a solubilizer and/or HPMC, wherein the solution has no visible solids.

In at least one embodiment, a stable intranasal pharmaceutical preparation comprises:
 (a) an aqueous solution of carbetocin, wherein the carbetocin is present in a concentration of about 10 mg/mL to about 70 mg/mL;
 (b) an amino acid, hydrotrope and/or HPMC; and
 (c) optionally an additional excipient, wherein the preparation has a pH ranging from about 3 to about 5.8.

In at least one embodiment, a stable intranasal pharmaceutical preparation comprises:
 (a) an aqueous solution of carbetocin, wherein the carbetocin is present in a concentration of about 1 mg/mL to about 70 mg/mL;
 (b) a hydrotrope selected from the group consisting of nicotinamide, sodium benzoate, and sodium salicylate; and
 (c) optionally an additional excipient. In another embodiment, the preparation has a pH ranging from about 3 to about 5.8.

In at least one embodiment, a stable intranasal pharmaceutical preparation comprises:
 (a) an aqueous solution of carbetocin, wherein the carbetocin is present in a concentration of about 1 mg/mL to about 70 mg/mL;
 (b) hydroxypropyl methylcellulose (HPMC), wherein the HPMC is present in an amount ranging from about 0.005% to 0.05% w/v; and
 (c) optionally an additional excipient, wherein the solution has a pH ranging from about 3 to about 5.8.

In at least one embodiment, a stable intranasal pharmaceutical preparation comprises:
 (a) an aqueous solution of carbetocin, wherein the carbetocin is present in a concentration of about 1 mg/mL to about 70 mg/mL;
 (b) nicotinamide;
 (c) HPMC; and
 (d) sorbitol, wherein the solution has a pH ranging from about 3 to about 5.8.

In at least one embodiment, a stable intranasal pharmaceutical preparation comprises:
 (a) an aqueous solution of carbetocin, wherein the carbetocin is present in a concentration of about 1 mg/mL to about 70 mg/mL;
 (b) methyl-β-cyclodextrin;
 (c) HPMC; and
 (d) sorbitol, wherein the solution has a pH ranging from about 3 to about 5.8.

In at least one embodiment, a stable intranasal pharmaceutical preparation comprises:
 (a) carbetocin, wherein the carbetocin is present in a concentration of about 25 mg/mL to about 35 mg/mL;
 (b) nicotinamide, wherein the nicotinamide is present in a concentration ranging from about 200 mM to about 400 mM;
 (c) HPMC, wherein the HPMC is present in an amount ranging from 0.0075% to 0.05% w/v; and
 (d) sorbitol, wherein the sorbitol is present in a concentration ranging from about 110 mM to about 250 mM.

In at least one embodiment, a stable intranasal pharmaceutical preparation comprises:
 (a) carbetocin, wherein the carbetocin is present in a concentration of about 34.3 mg/mL;
 (b) nicotinamide, wherein the nicotinamide is present in a concentration ranging from about 50 mM to about 500 mM;
 (c) HPMC, wherein the HPMC is present in an amount of about 0.01% w/v; and
 (d) sorbitol, and optionally an additional excipient chosen from EDTA, potassium sorbate, and combinations thereof.

In at least one embodiment, a stable intranasal pharmaceutical preparation comprises:
 (a) carbetocin, wherein the carbetocin is present in a concentration of about 11.4 mg/mL;
 (b) nicotinamide, wherein the nicotinamide is present in a concentration ranging from about 50 mM to about 500 mM;
 (c) HPMC, wherein the HPMC is present in an amount of about 0.01% w/v; and
 (d) sorbitol, and optionally an additional excipient chosen from EDTA, potassium sorbate, and combinations thereof.

In at least one embodiment, a stable intranasal pharmaceutical preparation comprises:
 (a) carbetocin, wherein the carbetocin is present in a concentration of about 1 mg/mL to about 4 mg/mL;
 (b) nicotinamide, wherein the nicotinamide is present in a concentration ranging from about 50 mM to about 500 mM;
 (c) HPMC, wherein the HPMC is present in an amount ranging from 0.01% to 0.05% w/v; and
 (d) sorbitol, wherein the sorbitol is present in a concentration ranging from about 100 mM to about 287 mM.

In at least one embodiment, the pharmaceutical preparations of the present disclosure are administered intranasally daily for a period of time. In at least one embodiment, the pharmaceutical preparations are administered intranasally up to 3 times daily for chronic use. In at least one embodiment, the pharmaceutical preparation is administered in a volume of about 50 μL to about 200 μL into one nostril and then a volume of about 50 μL to about 200 μL into the second nostril, for a combined volume of about 100 μL to about 400 μL for both nostrils. In at least one embodiment, the pharmaceutical preparations are administered intranasally 3 times daily for 20 consecutive days. In at least one embodiment, the pharmaceutical preparation is administered in a volume of about 20 μL to about 200 μL into one nostril and then a volume of about 20 μL to about 200 μL into the second nostril, for a combined volume of about 40 μL to about 400 μL for both nostrils. In at least one embodiment, the pharmaceutical preparation is administered in a volume of about 25 μL to about 35 μL into one nostril and then a volume of about 25 μL to about 35 μL into the second nostril, for a combined volume of about 50 μL to about 70 μL for both nostrils. In one embodiment, the pharmaceutical preparation is administered in a volume of 140 μL into one nostril and then a volume of 140 μL into the second nostril, for a combined volume of 280 μL for both nostrils.

In at least one embodiment, the pharmaceutical preparations of the present disclosure may be for use in (or in the manufacture of medicaments for) the treatment or prevention of a neurodevelopmental disorder or related symptoms in a subject in need thereof. In at least one embodiment, a therapeutically-effective amount of a pharmaceutical preparation of the present disclosure is administered to a subject diagnosed with Präder-Willi syndrome. In one embodiment, the pharmaceutical preparation is administered to the subject intranasally. In at least one embodiment, a total daily dose of carbetocin is from about 1 mg/day to about 30 mg/day. In at least one embodiment, a total daily dose of carbetocin is from about 8.0 mg/day to about 30.0 mg/day. In at least one embodiment, a total daily dose of carbetocin is from about 9.0 mg/day to about 29.0 mg/day. In one embodiment, a total daily dose of carbetocin is chosen from about 8.0 mg/day, about 9.0 mg/day, 10.0 mg/day, about 11.0 mg/day, about 12.0 mg/day, about 13.0 mg/day, about 14.0 mg/day, 15.0 mg/day. 16.0 mg/day, 17.0 mg/day, 18.0 mg/day, 19.0 mg/day, 20.0 mg/day, 21.0 mg/day, 22.0 mg/day, 23.0 mg/day, 24.0 mg/day, 25.0 mg/day, 26.0 mg/day, 27.0 mg/day, 28.0 mg/day, 29.0 mg/day, and about 30.0 mg/day. In another embodiment, a total daily dose of carbetocin is chosen from about 9.1 mg/day, about 9.2 mg/day, about 9.3 mg/day, about 9.4 mg/day, about 9.5 mg/day, about 9.6 mg/day, about 9.7 mg/day, about 9.8 mg/day, and about 9.9 mg/day. In at least one embodiment, a total daily dose of carbetocin is 9.6 mg/day. In one embodiment, a total daily dose of carbetocin is chosen from about 11.1 mg/day, about 11.2 mg/day, about 11.3 mg/day, about 11.4 mg/day, about 11.5 mg/day, about 11.6 mg/day, about 11.7 mg/day, about 11.8 mg/day, and about 11.9 mg/day. In at least one embodiment, a total daily dose of carbetocin is 11.4 mg/day. In one embodiment, a total daily dose of carbetocin is chosen from about 28.1 mg/day, about 28.2 mg/day, about 28.3 mg/day, about 28.4 mg/day, about 28.5 mg/day, about 28.6 mg/day, about 28.7 mg/day, about 28.8 mg/day, and about 28.9 mg/day. In at least one embodiment, a total daily dose of carbetocin is 28.8 mg/day. In at least one embodiment, the total daily dose is divided into 3 equal doses. In another embodiment, the pharmaceutical preparations disclosed show improved stability and bioavailability. In at least some embodiments, the pharmaceutical preparation is an aqueous solution of about 10 mg/mL to about 70 mg/mL carbetocin that includes a hydrotrope and a viscoelastic polymer in such concentrations that the solution retains 75-125% of the bioavailability (as measured by the area under the curve and the maximum concentration) of an aqueous solution of carbetocin in saline.

In another aspect, the disclosure provides a method of administering carbetocin to a subject diagnosed with Präder-Willi syndrome, wherein two or three doses per day of 3.2 mg/dose carbetocin are administered intranasally to the patient. According to this aspect, the disclosure provides a method of administering carbetocin to a subject diagnosed with Präder-Willi syndrome, wherein three doses per day of 3.2 mg/dose carbetocin are administered intranasally to the patient. The disclosure also provides a method of administering carbetocin to a subject diagnosed with Präder-Willi syndrome, wherein each dose is administered within 30 minutes of a meal or just before a meal. In another aspect, the disclosure provides a method of administering carbetocin to a subject diagnosed with Präder-Willi syndrome, wherein carbetocin is administered for at least one week, at least two weeks, at least three weeks, at least four weeks, at least one month, at least two months, at least three months, or longer.

The disclosure also provides a method of administering carbetocin to a subject diagnosed with Präder-Willi syndrome, wherein the administration results in one or more of (a) decrease in hyperphagia behavior compared to placebo, optionally as measured by the Hyperphagia Questionnaire for Clinical Trials (HQ-CT) Total Score; (b) decrease in obsessive and compulsive behavior compared to placebo, optionally as measured by the Children's Yale-Brown Obsessive-Compulsive Scale (CY-BOCS) Total Score; (c) decrease in anxiety compared to placebo, optionally as measured by the PWS Anxiety and Distress Questionnaire (PADQ) Total Score; and (d) improvement in global clinical impression compared to placebo, optionally as measured by the Clinical Global Impression of Change (CGI-C) score. According to this aspect, the disclosure provides a method of administering carbetocin to a subject diagnosed with Präder-Willi syndrome, wherein the administration results in a decrease in hyperphagia behavior. According to this aspect, the disclosure provides a method of administering carbetocin to a subject diagnosed with Präder-Willi syndrome, wherein the administration results in a decrease in hyperphagia behavior and a decrease in obsessive and compulsive behavior.

In another aspect, the disclosure provides a method of administering carbetocin to a subject diagnosed with Präder-Willi syndrome, wherein the age of the subject is from seven (7) to eighteen (18) years old, inclusive. According to this aspect, the disclosure provides a method of administering carbetocin to a subject diagnosed with Prader-Willi syndrome, wherein the subject is aged seven (7) years old, eight (8) years old, nine (9) years old, ten (10) years old, eleven (11) years old, twelve (12) years old, thirteen (13) years old, fourteen (14) years old, fifteen (15) years old, sixteen (16) years old, seventeen (17) years old, or eighteen (18) years old.

BRIEF DESCRIPTION OF DRAWINGS

The foregoing summary, as well as the following detailed description of the disclosure, will be better understood when read in conjunction with the appended drawings. For the purpose of illustrating the present disclosure, the attached drawings illustrate some, but not all, alternative embodiments. It should be understood, however, that the disclosure is not limited to the precise arrangements and instrumentalities shown. These figures, which are incorporated into and constitute part of the specification, assist in explaining the principles of the disclosure.

FIG. 3.(a) shows A350 measurements for samples having 80% headspace. FIG. 3.(b) shows A350 measurements for samples having limited headspace.

DETAILED DESCRIPTION OF THE DISCLOSURE

Figure 1:
FIG. 1. shows an example image comparing 400 mM and 200 mM sodium salicylate (left- and right-hand vials, respectively) samples after 6 days of continuous agitation. The 200 mM sample contains more and larger particles than the 400 mM sample. Additionally, the 200 mM sample has a slight opalescent appearance.

The present disclosure relates to a stable intranasal pharmaceutical preparation that comprises an aqueous solution of carbetocin and a solubilizer and/or HPMC. The pharmaceutical preparations disclosed may include but do not require a surfactant. The pharmaceutical preparations of the present disclosure exhibit improved stability despite their relatively high concentrations of carbetocin. For example, in certain embodiments, the pharmaceutical preparations show little to no visible solids after extended periods of time at room temperature. In other embodiments, the pharmaceutical preparations of the present disclosure exhibit little to no visible solids after shaking stress. The pharmaceutical preparations disclosed herein may be formulated in a container having reduced headspace, which may include close to or substantially zero headspace to minimize, for example, the gas-water interface. In certain embodiments, however, it is unnecessary to reduce headspace to maintain improved stability. The pharmaceutical preparations disclosed exhibit improved stability despite their relatively high concentrations of carbetocin (e.g., ≥10 mg/mL). Certain embodiments are stable under conditions of stress, such as mechanical stress (e.g., shaking and stirring, pumping, freeze-thaw processes). The pharmaceutical preparations of the present disclosure also possess advantageously extended in-use time and/or shelf life for the patient. For example, the pharmaceutical preparation of the present disclosure exhibits an in-use time ranging from 1 day to 7 days, and includes embodiments wherein the content uniformity of carbetocin remains consistent and high throughout the in-use period. In some embodiments, the pharmaceutical preparations of the present disclosure also possess good local tolerability after 14 days at room temperature. In at least some embodiments, the pharmaceutical preparations of the present disclosure possess good local tolerability for 3-7 days at room temperature.

In at least one embodiment, the present disclosure is directed to a stable pharmaceutical preparation comprising an aqueous solution of carbetocin and a solubilizer and/or a viscoelastic polymer, such as HPMC, wherein the concentration of carbetocin ranges from about 1 mg/mL to about 70 mg/mL. In at least some embodiments, the addition of HPMC to the preparation reduces aggregation of an aqueous solution of carbetocin compared to an aqueous solution of carbetocin that does not contain HPMC. In some embodiments, the HPMC in the carbetocin preparation reduces aggregation of the carbetocin solution by at least 20% and up to 50% when compared to an aqueous solution of carbetocin that does not contain HPMC. In other embodiments, the HPMC in the carbetocin preparation reduces aggregation of the carbetocin solution by at least 20% compared to an aqueous solution of carbetocin that does not contain HPMC. In some embodiments, the HPMC in the carbetocin preparation reduces aggregation of the carbetocin solution by at least 30% compared to an aqueous solution of carbetocin that does not contain HPMC. In some embodiments, the HPMC in the carbetocin preparation reduces aggregation of the carbetocin solution by at least 40% compared to an aqueous solution of carbetocin that does not contain HPMC. In some embodiments, the HPMC in the carbetocin preparation reduces aggregation of the carbetocin solution by at least 50% compared to an aqueous solution of carbetocin that does not contain HPMC.

For example, the concentration of carbetocin ranges from 1 mg/mL to 70 mg/mL, such as from 5 to 65 mg/mL, from 10 mg/mL to 50 mg/mL, from 15 mg/mL to 35 mg/mL, or from 30 mg/mL to 34 mg/mL. In at least one embodiment, the concentration of carbetocin in solution is about 40 mg/mL. In another embodiment, the concentration of carbetocin ranges from about 10 mg/mL to about 45 mg/mL. In at least one embodiment, the concentration of carbetocin ranges from about 20 mg/mL to about 40 mg/mL. In at least one embodiment, the concentration of carbetocin may be, for example, about 10 mg/mL, about 15 mg/mL, about 20 mg/mL, about 25 mg/mL, about 30 mg/mL, about 33 mg/mL, about 34 mg/mL, about 35 mg/mL, 36 mg/mL, about 37 mg/mL, about 38 mg/mL, about 39 mg/mL, or about 40 mg/mL. In another embodiment, the concentration of carbetocin may be, for example, 34.1 mg/mL, 34.2 mg/mL, 34.3 mg/mL, 34.4 mg/mL, 34.5 mg/mL, 34.6 mg/mL, 34.7 mg/mL, 34.8 mg/mL, 34.9 mg/mL, or 40 mg/mL. In one embodiment, the concentration of carbetocin is about 34.3 mg/mL.

For the pharmaceutical preparations of the present disclosure at least one solubilizer and/or HPMC is included in the pharmaceutical preparation.

In at least one embodiment, the hydrotrope is an aromatic anionic compound, an aromatic cationic compound, or aliphatic and linear compounds. Examples of hydrotropes include but are not limited to nicotinamide, sodium benzoate, salicylate salts (e.g., sodium salicylate, potassium salicylate, lithium salicylate, ammonium salicylate, calcium salicylate, magnesium salicylate etc.), N,N-diethylnicotinamide, or N,N-dimethyl benzamide. In certain embodiments, the hydrotrope is nicotinamide, sodium benzoate, or sodium salicylate. The hydrotrope may also be an aromatic cationic compound, such as caffeine and procaine hydrochloride. In other embodiments, the hydrotrope may be an aliphatic and linear compound chosen from N,N-dimethyl urea, urea, or sodium alkanoate.

If present in the pharmaceutical preparation, nicotinamide is present in a concentration ranging from 50 mM to 500 mM. In at least one embodiment, the nicotinamide concentration ranges from about 50 mM to about 350 mM, such as from 100 mM to 220 mM, from 240 mM to 260 mM, from 280 mM to 300 mM, or from 320 mM to 340 mM. In at least one embodiment, the concentration of nicotinamide is, for example, about 200 mM, about 210 mM, about 220 mM, about 230 mM, about 240 mM, about 250 mM, about 260 mM, about 270 mM, about 280 mM, about 290 mM, about 300 mM, about 310 mM, about 320 mM, about 330 mM, about 340 mM, about 350 mM, about 360 mM, about 370 mM, about 380 mM, about 290 mM, or about 400 mM. In at least one embodiment, the concentration of nicotinamide is about 400 mM. In at least one embodiment, the concentration of nicotinamide is about 350 mM. In at least one embodiment, the concentration of nicotinamide is about 300 mM. In at least one embodiment, the concentration of nicotinamide is about 250 mM. In another embodiment, the concentration of nicotinamide is about 200 mM.

If present in the pharmaceutical preparation, the sodium salicylate salt (e.g., sodium salicylate, potassium salicylate, lithium salicylate, ammonium salicylate, calcium salicylate, magnesium salicylate etc.) is present in a concentration ranging from 50 mM to 500 mM. In at least some embodiments, the salicylate salt is sodium salicylate which is present in a concentration ranging from 200 mM to 400 mM. In at least one embodiment, the sodium salicylate concentration ranges from about 200 mM to about 300 mM, such as from 200 mM to 220 mM, from 240 mM to 260 mM, or from 280 mM to 300 mM. In at least one embodiment, the concentration of sodium salicylate is about 400 mM. In at least one embodiment, the concentration of sodium salicylate is about 300 mM. In another embodiment, the concentration of sodium salicylate is about 200 mM.

If present in the pharmaceutical preparation, sodium benzoate is present in a concentration ranging from 100 mM to 400 mM. In at least one embodiment, the sodium benzoate concentration ranges from about 160 mM to about 400 mM, such as from 160 mM to 200 mM, from 250 mM to 300 mM, or from 350 mM to 400 mM. In at least one embodiment, the concentration of sodium benzoate is about 160 mM. In at least one embodiment, the concentration of sodium benzoate is about 400 mM.

If present in the pharmaceutical preparation, methyl-β-cyclodextrin is present in a concentration ranging from 15 mM to 50 mM. In at least one embodiment, the methyl-β-cyclodextrin concentration ranges from about 17.5 mM to about 40 mM, such as from 17.5 mM to 25 mM, from 30 mM to 35 mM, or from 35 mM to 40 mM. In at least one embodiment, the concentration of methyl-β-cyclodextrin is about 17.5 mM. In at least one embodiment, the concentration of methyl-β-cyclodextrin is about 2.5 mM. In at least one embodiment, the concentration of methyl-β-cyclodextrin is about 35 mM.

If present in the pharmaceutical preparation, HPMC is present in an amount ranging from 0.005% to 0.05% w/v. In at least one embodiment, HPMC is present in an amount ranging from 0.0075% to 0.0125% w/v. In another embodiment, HPMC is present in an amount ranging from 0.0075% to 0.01% w/v. In at least one embodiment, HPMC is present in an amount of 0.01% w/v. In at least one embodiment, the grade of HPMC is chosen from low viscosity (e.g., 10-20 cP), medium viscosity (e.g., 40-60 cP), and high viscosity (e.g., 80-120 cP, 4000 cP). In at least one embodiment, HPMC is high viscosity grade. In at least one embodiment, the high viscosity HPMC possesses a viscosity of 4000 cP.

The pharmaceutical preparations of the present disclosure may include a solubilizer and HPMC. Thus, in certain embodiments, nicotinamide, sodium benzoate, sodium salicylate, arginine, methyl-β-cyclodextrin, and combinations thereof are present in the pharmaceutical preparation with HPMC. Such preparations may optionally contain an additional excipient. Non-limiting examples of additional excipients include sorbitol, ethylenediaminetetraacetic acid (EDTA), potassium sorbate, mannitol, and sodium or potassium acetate. These additional excipients may be included even if only a solubilizer or HPMC is present alone. Specifically, in at least one embodiment, the pharmaceutical preparation contains at least one solubilizer or HPMC with at least one additional excipient.

In some embodiments, the presence of either HPMC or nicotinamide alone in the carbetocin formulation may be sufficient to mitigate precipitation of carbetocin upon prolonged agitation. This is possible because HPMC and nicotinamide have independent mechanisms of action. It was found that HPMC associates to the glass surface of the vial and because of this association it can minimize the interaction of carbetocin with this interface. In contrast, it was surprisingly found that nicotinamide is able to solubilize aggregates formed during agitation, which in turn reduces carbetocin's propensity to aggregate and subsequently form small and large precipitates. It was further found that the addition of both nicotinamide and HPMC to a carbetocin preparation results in a synergistic effect that blocks, reduces, or prevents carbetocin from aggregating and subsequently precipitating in solution. The resulting carbetocin preparations comprising nicotinamide and HPMC are surprisingly stable under accelerated conditions of stress for long periods of time.

In at least some embodiments, the present disclosure is directed to a stable intranasal pharmaceutical preparation comprising an aqueous solution of carbetocin and a solubilizer and/or surface active agent, such as HPMC, wherein the resulting preparation shows a surprising high content uniformity of carbetocin for long periods of time and after one or more freeze/thaw cycles. For example, the disclosed preparations show content uniformity of carbetocin after one or more freeze/thaw cycles for a duration chosen from 1 day, 2 days, 3 days, 4 days, 5 days, 6 days, and 7 days. In at least some embodiments, the pharmaceutical preparation has little to no aggregates by visual assessment after thawing for up to 7 days. In some embodiments, the carbetocin in the disclosed preparation is evenly distributed throughout the preparation to ensure that if the preparation is, for example, split in one or more preparations, each resulting preparation has an equal dose of carbetocin. In one embodiment, the disclosed carbetocin preparations have a consistent dose of carbetocin, which is maintained between various preparation batches so that the patient receives the correct dose consistently over various administrations. In at least one embodiment, the disclosed carbetocin preparation provides enhanced convenience and patient compliance.

A tonicity enhancer/modifier may be, but is not required, to provide isotonic formulations (e.g., 300 mOsm/Kg). In at least one embodiment, the osmolality of a pharmaceutical composition is preferably adjusted to maximize the active ingredient's stability and/or to minimize discomfort to the patient upon administration. In at least one embodiment, the pharmaceutical composition for direct administration to a patient is isotonic, which may be achieved by addition of a tonicity modifier, such as sorbitol. Other non-limiting examples of tonicity modifiers include amino acids (e.g., cysteine, arginine, histidine, glycine etc.), salts (e.g., sodium chloride, potassium chloride, sodium citrate etc.) or non-electrolytes (e.g., sugars or polyols, such as, for example, sucrose, glucose and mannitol).

If present in the pharmaceutical preparation of the present disclosure, the tonicity enhancer/modifier is added to adjust the osmolality to, for example, about 225 mOsm/Kg, about 226 mOsm/Kg, about 227 mOsm/Kg, about 228 mOsm/Kg, about 229 mOsm/Kg, about 230 mOsm/Kg, about 231 mOsm/Kg, about 232 mOsm/Kg, about 233 mOsm/Kg, about 234 mOsm/Kg, about 235 mOsm/Kg, about 236 mOsm/Kg, about 237 mOsm/Kg, about 238 mOsm/Kg, about 239 mOsm/Kg, about 240 mOsm/Kg, about 241 mOsm/Kg, about 242 mOsm/Kg, about 243 mOsm/Kg, about 244 mOsm/Kg, about 245 mOsm/Kg, about 246 mOsm/Kg, about 247 mOsm/Kg, about 248 mOsm/Kg, about 249 mOsm/Kg, about 250 mOsm/Kg, about 251 mOsm/Kg, about 252 mOsm/Kg, about 253 mOsm/Kg, about 254 mOsm/Kg, about 255 mOsm/Kg, about 256 mOsm/Kg, about 257 mOsm/Kg, about 258 mOsm/Kg, about 259 mOsm/Kg, about 260 mOsm/Kg, about 261 mOsm/Kg, about 262 mOsm/Kg, about 263 mOsm/Kg, about 264 mOsm/Kg, about 265 mOsm/Kg, about 266 mOsm/Kg, about 267 mOsm/Kg, about 268 mOsm/Kg, about 269 mOsm/Kg, about 270 mOsm/Kg, about 271 mOsm/Kg, about 272 mOsm/Kg, about 273 mOsm/Kg, about 274 mOsm/Kg, about 275 mOsm/Kg, about 276 mOsm/Kg, about 277 mOsm/Kg, about 278 mOsm/Kg, about 279 mOsm/Kg, about 280 mOsm/Kg, about 281 mOsm/Kg, about 282 mOsm/Kg, about 283 mOsm/Kg, about 284 mOsm/Kg, about 285 mOsm/Kg, about 286 mOsm/Kg, about 287 mOsm/Kg, about 288 mOsm/Kg, about 289 mOsm/Kg, about 290 mOsm/Kg, about 291 mOsm/Kg, about 292 mOsm/Kg, about 293 mOsm/Kg, about 294 mOsm/Kg, about 295 mOsm/Kg, about 296 mOsm/Kg, about 297 mOsm/Kg, about 298 mOsm/Kg, about 299 mOsm/Kg, about 300 mOsm/Kg, about 310 mOsm/Kg, about 320 mOsm/Kg, about 330 mOsm/Kg, about 340 mOsm/Kg, about 350 mOsm/Kg, about 360 mOsm/Kg, about 370 mOsm/Kg, about 380 mOsm/Kg, about 390 mOsm/Kg, about 400 mOsm/Kg, about 410 mOsm/Kg, about 420 mOsm/Kg, about 430 mOsm/Kg, about 440 mOsm/Kg, about 450 mOsm/Kg, about 460 mOsm/Kg, about 470 mOsm/Kg, about 480 mOsm/Kg, about 490 mOsm/Kg, about 500 mOsm/Kg, about 510 mOsm/Kg, about 520 mOsm/Kg, about 530 mOsm/Kg, about 540 mOsm/Kg, about 550 mOsm/Kg, about 560 mOsm/Kg, about 570 mOsm/Kg, about 580 mOsm/Kg, about 600 mOsm/Kg, about 610 mOsm/Kg, about 620 mOsm/Kg, about 630 mOsm/Kg, about 640 mOsm/Kg, about 650 mOsm/Kg, about 660 mOsm/Kg, about 670 mOsm/Kg, about 680 mOsm/Kg, about 700 mOsm/Kg, about 710 mOsm/Kg, about 720 mOsm/Kg, about 730 mOsm/Kg, about 740 mOsm/Kg, about 750 mOsm/Kg, about 760 mOsm/Kg, about 770 mOsm/Kg, about 780 mOsm/Kg, or about 800 mOsm/Kg. In some embodiments, the osmolality may be in excess of 800 mOsm/Kg.

In some embodiments, sorbitol is present in a concentration ranging from 100 mM to 300 mM. In some embodiments, sorbitol is present in a concentration ranging from 110 mM to 287 mM. In some embodiments, sorbitol is added to adjust the osmolality to, for example, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, about 195 mM, about 200 mM, 205 mM, about 210 mM, about 215 mM, about 220 mM, about 225 mM, about 230 mM, about 235 mM, about 240 mM, about 245 mM, about 250 mM, about 255 mM, about 260 mM, 265 mM, about 270 mM, about 275 mM, about 280 mM, about 285 mM, about 290 mM, or about 300 mM. In at least one embodiment, the concentration of sorbitol is chosen from about 110 mM, about 120 mM, about 150 mM, about 200 mM, about 250 mM, or about 287 mM. In at least one embodiment, the concentration of sorbitol is about 110 mM. In at least one embodiment, the concentration of sorbitol is about 130 mM.

This disclosure is also directed to achieving a stable lyophilized preparation of carbetocin. In at least one embodiment, a carbetocin lyophilisate is mixed with a solubilizer and/or HPMC in water to obtain a pharmaceutical preparation drug product. Without being bound to any particular theory, the solubilizer and/or HPMC expedites dissolution of lyophilized carbetocin as compared to its typically slow reconstitution with conventional diluents (e.g., bulking agents and sugar stabilizers). In at least one embodiment, isotonic solutions comprising a solubilizer and/or HPMC of the disclosure efficiently solubilize carbetocin lyophilizate. In one embodiment, isotonic solutions of, for example, arginine and/or nicotinamide (a hydrotrope) efficiently solubilize carbetocin lyophilizate. In at least one embodiment, the solubilizer and/or HPMC of the disclosure increases the dissolution rate of lyophilized carbetocin. In at least one embodiment, the solubilizer is nicotinamide which improves the dissolution rate of lyophilized carbetocin. The use of a solubilizer, such as nicotinamide and/or HPMC, reduced the dissolution time of the lyophilized carbetocin (at 40 mg/mL) to only a few minutes, a time generally considered acceptable for a lyophilized drug product.

In at least one embodiment, the solubilizer is an arginine salt (e.g., HCl salt). In some embodiments, the arginine salt is present in the pharmaceutical preparation in a concentration ranging from 50 mM to 300 mM. In at least one embodiment, the arginine concentration ranges from about 100 mM to about 300 mM, such as from 100 mM to 150 mM, from 200 mM to 250 mM, or from 250 mM to 300 mM. In at least one embodiment, the concentration of arginine salt is about 100 mM. In at least one embodiment, the concentration of arginine salt is about 200 mM.

In at least one embodiment, the solubilizer is nicotinimide. In some embodiments, the nicotinimide is present in the pharmaceutical preparation in a concentration ranging from 50 mM to 500 mM. In at least one embodiment, the nicotinimide concentration ranges from about 50 mM to about 350 mM, such as from 200 mM to 220 mM, from 240 mM to 280 mM, or from 300 mM to 350 mM. In at least one embodiment, the concentration of nicotinimide is about 200 mM. In at least one embodiment, the concentration of nicotinamide is about 300 mM. In at least one embodiment, the concentration of nicotinimide is about 400 mM.

In at least one embodiment, the solubilizer is methyl-β-cyclodextrin. In some embodiments, the methyl-β-cyclodextrin is present in the pharmaceutical preparation in a concentration ranging from 10 mM to 40 mM. In at least one embodiment, the methyl-β-cyclodextrin concentration ranges from about 15 mM to about 35 mM, such as from 17.5 mM to 19.5 mM, from 24 mM to 28 mM, or from 30 mM to 35 mM. In at least one embodiment, the concentration of methyl-β-cyclodextrin is about 35 mM. In at least one embodiment, the concentration of methyl-β-cyclodextrin is about 25 mM. In at least one embodiment, the concentration of methyl-β-cyclodextrin is about 17.5 mM.

This disclosure is further directed to a pharmaceutical preparation comprising an aqueous solution of carbetocin and a solubilizer and/or HPMC in a container, wherein the headspace in the container is near zero (i.e., limited headspace). In another embodiment, such a pharmaceutical preparation with reduced headspace does not include a surfactant. That is, the present disclosure includes a pharmaceutical preparation comprising an aqueous solution of carbetocin and a solubilizer, and/or optionally HPMC in a container, wherein the headspace in the container is near zero, and wherein the preparation is substantially free of a surfactant (e.g., non-ionic surfactant, such as n-dodecyl-β-D-maltoside (DDM), poloxamer 188, polysorbate 20 or polysorbate 80), for example, such that the pharmaceutical preparation does not include a surfactant. In at least one embodiment, a surface active agent is not present in the preparation disclosed.

The term "headspace" is a term well understood in the art and refers to gas space within a sealed container containing a solution. The volume of the headspace may vary depending on the entire inner volume of the container and the amount of solution it contains.

For example, in at least one embodiment, the headspace represents about 2.0 mL, 1.9 mL, 1.8 mL, 1.7 mL, 1.6 mL, 1.5 mL, 1.4 mL, 1.3 mL, 1.2 mL, 1.1 mL, 1.0 mL, 0.9 mL, about 0.8 mL, about 0.7 mL, about 0.6 mL, about 0.5 mL, about 0.4 mL, about 0.3 mL, about 0.2 mL, about 0.18 mL, about 0.15 mL, about 0.12 mL, about 0.1 mL, about 0.08 mL, about 0.07 mL, about 0.06 mL, about 0.05 mL, about 0.04 mL, about 0.03 mL, about 0.020 mL, or about 0.01 mL of the volume of the container comprising the carbetocin solution. In at least one embodiment, the headspace represents about 80%, about 70%, about 60%, about 50%, about 45%, about 40%, about 35%, about 30%, about 25%, about 20%, about 15%, about 12%, about 10%, about 9%, about 8%, about 7%, about 6%, about 5%, about 4%, about 3%, about 2%, about 1.5%, about 1%, about 0.75%, about 0.5%, about 0.25%, or about 0.1% of the volume of the container comprising the carbetocin solution. In at least one embodiment, the headspace represents less than 0.5%, less than 0.4%, less than 0.3%, less than 0.2%, less than 0.1%, less than 0.001%, or 0.0% of the total volume of the container. In at least one embodiment of the present disclosure, the container headspace is substantially zero.

The pharmaceutical preparations of the present disclosure are advantageous because they may be stable even at high concentrations of carbetocin, such as at a concentration ranging from about 10 mg/mL to about 70 mg/mL, including about 34 mg/mL.

In at least one embodiment, the stability of the pharmaceutical preparation is evident because it resists aggregate formation, and the aqueous solution has little to no visible solids (e.g., particles). In some embodiments, the carbetocin in solution has little to no visible solids when stored at room temperature (~25° C.) for a sustained period of time. For example, in some embodiments, the carbetocin solution has little to no visible solids for up to 5 years. In some embodiments, the carbetocin solution has little to no visible solids for up to 4 years. In some embodiments, the carbetocin solution has little to no visible solids for up to 3 years. In some embodiments, the concentration of carbetocin in the aqueous solution does not change over time (e.g., over 3, 4, or 5 years).

The pharmaceutical preparations of the present disclosure remain stable to shaking stress. For example, the aqueous carbetocin solution is stable to shaking stress for a period of time. In some embodiments, the preparation is subjected to constant shaking stress for 14 days at both 5° C. and 25° C. (e.g., 200 or more RPMs), and the aqueous carbetocin solution remains clear with little to no visible particles. In some embodiments, the preparation is subjected to shaking stress for 1, 2, 3, 4, 5, 6, or 7 days at both 5° C. and 25° C., and the aqueous carbetocin solution remains clear with little to no visible particles. In at least one embodiment, the preparation is subjected to shaking stress for 5 days, and the aqueous carbetocin solution remains clear with little to no visible particles. In some embodiments, the preparation is subjected to shaking stress for at least 3 days, and the aqueous carbetocin solution remains clear with little to no visible particles. In at least one embodiment, the pharmaceutical preparations are stable to shaking stress for at least 1 hour, 2 hours, 3 hours, 4 hours, 5 hours, 6 hours, 7 hours, 8 hours, 9 hours, 10 hour, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, or 48 hours, and the aqueous carbetocin solution remains clear with little to no visible particles.

The stability of the pharmaceutical preparations described herein may also be measured by the chromatographic purity of carbetocin. In at least one embodiment, controls at one or more days assure that chromatographic purity of carbetocin is greater than 95%. In at least one embodiment, controls at one or more days assure that chromatographic purity of carbetocin is greater than 96%. In at least one embodiment, controls at one or more days assure that chromatographic purity of carbetocin is greater than 97%. In at least one embodiment, the chromatographic purity of carbetocin is greater than 98%. In at least one embodiment, the chromatographic purity of carbetocin is greater than 99%. In at least one embodiment, the chromatographic purity of carbetocin is greater than 99.4%. In at least one embodiment, the chromatographic purity of carbetocin is greater than 99.5%. In at least one embodiment, the chromatographic purity of carbetocin is greater than 99.6%. In at least one embodiment, the chromatographic purity of carbetocin is greater than 99.7%. In at least one embodiment, the chromatographic purity of carbetocin is greater than 99.8%. In at least one embodiment, the chromatographic purity of carbetocin is greater than 99.9%. In at least one embodiment, carbetocin is not subject to chemical degradation, i.e., there is minimal or no change in chromatographic purity of carbetocin before or after shaking stress. In addition, the pharmaceutical preparations of the present disclosure exhibit stability in that the concentration of carbetocin in solution does not change over time, including under conditions of shaking stress.

In at least one embodiment, the chromatographic purity of carbetocin in solution with a solubilizer and/or surface active agent disclosed is greater than 98% after 24 hours of stress. In at least one embodiment, the chromatographic purity of carbetocin in solution with a solubilizer and/or surface active agent disclosed is greater than 98% after 36 hours of stress. In at least one embodiment, the chromatographic purity of carbetocin in solution with a solubilizer and/or surface active agent disclosed is greater than 98% at 48 hours of stress. In at least one embodiment, the chromatographic purity of carbetocin in solution a solubilizer and/or surface active agent disclosed is greater than 98% at 72 hours of stress.

In at least one embodiment, the chromatographic purity of carbetocin in solution with a solubilizer and/or surface active agent disclosed is greater than 99% after 24 hours of stress. In at least one embodiment, the chromatographic purity of carbetocin in solution with a solubilizer and/or surface active agent disclosed is greater than 99% after 36 hours of stress. In at least one embodiment, the chromatographic purity of carbetocin in solution with a solubilizer and/or surface active agent disclosed is greater than 99% at 48 hours of stress. In at least one embodiment, the chromatographic purity of carbetocin in solution with a solubilizer and/or surface active agent disclosed is greater than 99% at 72 hours of stress.

In at least one embodiment, the chromatographic purity of carbetocin in solution with a solubilizer and/or surface active agent disclosed is greater than 99.5% after 24 hours of stress. In at least one embodiment, the chromatographic purity of carbetocin in solution with a solubilizer and/or surface active agent disclosed is greater than 99.5%. after 36 hours of stress. In at least one embodiment, the chromatographic purity of carbetocin in solution with a solubilizer and/or surface active agent disclosed is greater than 99.5% at 48 hours of stress. In at least one embodiment, the chromatographic purity of carbetocin in solution with a solubilizer and/or surface active agent disclosed is greater than 99.5% at 72 hours of stress.

In general, the pharmaceutical preparations of the present disclosure will have a pH from about 3.0 to about 5.8. In at least one embodiment, the pH of the aqueous carbetocin solution may be from 3.5 to 5.7, for example from 4.2 to 5.6, or for example from 5.3 to 5.4. In some embodiments of the present disclosure, the pH of the pharmaceutical preparation is from about 5.3 to about 5.5; about 5.3±3; 5.4±3; or 5.5±3. In at least one embodiment, the pH of the aqueous carbetocin solution is 5.4±0.5. In another embodiment, the pH of the aqueous carbetocin solution is 5.4±0.3. In another embodiment, the pH of the aqueous carbetocin solution is 5.4±0.1.

The pharmaceutical preparations of the present disclosure may include a container. Non-limiting examples of a container include an ampoule, vial, pre-filled filed intranasal dispenser. In at least one embodiment, the container is an ampoule or a vial. In at least one embodiment, the container is a vial.

Exemplary Pharmaceutical Preparations

In at least one embodiment, a stable intranasal pharmaceutical preparation comprises:
(a) an aqueous solution of carbetocin, wherein the concentration of carbetocin ranges from about 10 mg/mL to about 70 mg/mL; and
(b) a solubilizer and/or HPMC, wherein the solution has no visible solids.

In at least one embodiment, a stable intranasal pharmaceutical preparation comprises:
(a) an aqueous solution of carbetocin, wherein the carbetocin is present in a concentration of about 10 mg/mL to about 70 mg/mL;
(b) an amino acid, hydrotrope, and/or HPMC; and
(c) optionally an additional excipient, wherein the preparation has a pH ranging from about 3 to about 5.8.

In at least one embodiment, a stable intranasal pharmaceutical preparation comprises:
(a) an aqueous solution of carbetocin, wherein the carbetocin is present in a concentration of about 1 mg/mL to about 70 mg/mL;
(b) a hydrotrope selected from the group consisting of nicotinamide, sodium benzoate, and sodium salicylate; and
(c) optionally an additional excipient. In another embodiment, the preparation has a pH ranging from about 3 to about 5.8.

In at least one embodiment, a stable intranasal pharmaceutical preparation comprises:
(a) an aqueous solution of carbetocin, wherein the carbetocin is present in a concentration of about 1 mg/mL to about 70 mg/mL;
(b) hydroxypropyl methylcellulose (HPMC), wherein the HPMC is present in an amount ranging from 0.005% to 0.05% w/v; and
(c) optionally an additional excipient, wherein the solution has a pH ranging from about 3 to about 5.8.

In at least one embodiment, a stable intranasal pharmaceutical preparation comprises:
(a) an aqueous solution of carbetocin, wherein the carbetocin is present in a concentration of about 1 mg/mL to about 70 mg/mL;
(b) nicotinamide;
(c) HPMC; and
(d) sorbitol, wherein the solution has a pH ranging from about 5 to about 5.8.

In at least one embodiment, a stable intranasal pharmaceutical preparation comprises:
(a) an aqueous solution of carbetocin, wherein the carbetocin is present in a concentration of about 1 mg/mL to about 70 mg/mL;
(b) methyl-β-cyclodextrin;
(c) HPMC; and
(d) sorbitol, wherein the solution has a pH ranging from about 5 to about 5.8.

In at least one embodiment, a stable intranasal pharmaceutical preparation comprises:
(a) carbetocin, wherein the carbetocin is present in a concentration of about 25 mg/mL to about 35 mg/mL;
(b) nicotinamide, wherein the nicotinamide is present in a concentration ranging from about 50 mM to about 500 mM;
(c) HPMC, wherein the HPMC is present in an amount ranging from 0.0075% to 0.05% w/v; and
(d) sorbitol, wherein the sorbitol is present in a concentration ranging from about 110 mM to about 250 mM.

In at least one embodiment, a stable intranasal pharmaceutical preparation comprises:
(a) carbetocin, wherein the carbetocin is present in a concentration of about 34.3 mg/mL;
(b) nicotinamide, wherein the nicotinamide is present in a concentration ranging from about 50 mM to about 500 mM;
(c) HPMC, wherein the HPMC is present in an amount of about 0.01% w/v; and
(d) sorbitol, and optionally an additional excipient chosen from EDTA, potassium sorbate, and combinations thereof.

In at least one embodiment, a stable intranasal pharmaceutical preparation comprises:
(a) carbetocin, wherein the carbetocin is present in a concentration of about 11.4 mg/mL;
(b) nicotinamide, wherein the nicotinamide is present in a concentration ranging from about 50 mM to about 500 mM;
(c) HPMC, wherein the HPMC is present in an amount of about 0.01% w/v; and
(d) sorbitol, and optionally an additional excipient chosen from EDTA, potassium sorbate, and combinations thereof.

In at least one embodiment, a stable intranasal pharmaceutical preparation comprises:
(a) carbetocin, wherein the carbetocin is present in a concentration of about 1 mg/mL to about 4 mg/mL;
(b) nicotinamide, wherein the nicotinamide is present in a concentration ranging from about 50 mM to about 500 mM;
(c) HPMC, wherein the HPMC is present in an amount ranging from 0.01% to 0.05% w/v; and
(d) sorbitol, wherein the sorbitol is present in a concentration ranging from about 100 mM to about 287 mM.

In each of these exemplary embodiments, the headspace of the container may optionally be reduced. In addition, the headspace may be substantially zero for each of these exemplary embodiments.

The pharmaceutical preparations disclosed herein may optionally include one or more pharmaceutically acceptable solvents. In at least one embodiment, the one or more solvents may be present as a mixture with water, such as, for example, a pharmaceutically acceptable alcohol and water.

The present disclosure also provides for a kit of parts comprising: a liquid (e.g., aqueous) pharmaceutical composition comprising carbetocin with a solubilizer and/or a surface active agent, wherein the pH of the composition is from 3.0 to 5.8; and a container for the composition, optionally with separate injection means (e.g., if required for administration), optionally with instructions for administration of the composition. The pH of the composition may be from 3.5 to 5.75, for example from 4.0 to 5.65. The pH of the composition may be from 5.15 to 5.75, for example from 5.2 to 5.65. The pH of the composition may be from 5.30 to 5.8, for example from 5.40 to 5.70, for example from 5.50 to 5.6. In at least one embodiment, the pH of the composition is about 5.4. In at least one embodiment, the pH of the aqueous carbetocin solution is 5.4±0.5. In another embodiment, the pH of the aqueous carbetocin solution is 5.4±0.3. In another embodiment, the pH of the aqueous carbetocin solution is 5.4±0.1. In at least one embodiment, the pH of the pharmaceutical composition is adjusted to the desired pH (e.g., 5.4) by addition of an appropriate amount of a base. In one embodiment the base is NaOH. In at least one embodiment, the base is 5 M NaOH.

Methods of Preparation

In at least one embodiment, the present disclosure provides a method to prepare a pharmaceutical preparation of carbetocin that has a relatively high concentration carbetocin and which demonstrates improved stability at room temperature and/or under conditions of stress. In at least one embodiment, a stable pharmaceutical preparation of aqueous carbetocin is prepared, for example, in a container. In at least one embodiment, the disclosure provides a method for preparing a stable pharmaceutical preparation of aqueous carbetocin and a container, wherein the concentration of carbetocin ranges from about 10 mg/mL to about 70 mg/mL, comprising: (a) adding aqueous carbetocin solution to the container, and optionally the added solution can be in an amount sufficient to reduce headspace (e.g., 20% headspace, 10% headspace, 5% headspace, close to zero headspace (i.e., limited headspace)); and (b) adding a solubilizer and/or HPMC to the solution. In at least one embodiment, the pharmaceutical preparation of aqueous carbetocin prepared by the method disclosed herein has little to no visible solids after horizontal shaking for 24 hours. In at least one embodiment, the pharmaceutical preparation of aqueous carbetocin prepared by the method disclosed herein has little to no visible solids after horizontal shaking for 48 hours. In at least one embodiment, the pharmaceutical preparation of aqueous carbetocin prepared by the method disclosed herein has little to no visible solids after horizontal shaking for 72 hours. In at least one embodiment, the pharmaceutical preparation of aqueous carbetocin prepared by the method disclosed herein has little to no visible solids after horizontal shaking for 96 hours. In at least one embodiment, carbetocin is not subject to chemical degradation before or after the shaking stress. In at least one embodiment, controls at one or more days assure that chromatographic purity of carbetocin is greater than 98%. In at least one embodiment, the chromatographic purity of carbetocin is greater than 99%. In at least one embodiment, the chromatographic purity of carbetocin is 99.4±0.0%. In at least one embodiment, the chromatographic purity of carbetocin is 99.4±0.1%. In at least one embodiment, the chromatographic purity of carbetocin is 99.4±0.2%. In at least one embodiment, the chromatographic purity of carbetocin is 99.5±0.0%. In at least one embodiment, the chromatographic purity of carbetocin is 99.5±0.1%. In at least one embodiment, the chromatographic purity of carbetocin is 99.5±0.2%. In at least one embodiment, the chromatographic purity of carbetocin is 99.8±0.3%. In at least one embodiment, the chromatographic purity of carbetocin is 99.9±0.1%.

Methods of Treatment

In at least one embodiment, the disclosure provides a method of treating a subject suffering from, or susceptible to, a disease that is beneficially treated by a stable high concentration pharmaceutical preparation of carbetocin comprising the step of administering to said subject an effective amount of a pharmaceutical preparation of the present disclosure.

In at least one embodiment, the pharmaceutical preparations of the present disclosure may be for use in (or in the manufacture of medicaments for) the treatment or prevention of neurodevelopmental disorders, including Präder-Willi syndrome, or related symptoms in a mammalian subject in need thereof. In at least one embodiment, a therapeutically-effective amount of a pharmaceutical preparation of the present disclosure is administered to a subject suffering from Präder-Willi syndrome.

EXAMPLES

The present disclosure may be better understood by reference to examples. The following examples are intended for illustration purposes only and should not be construed as limiting the scope of the disclosure in any way. Further, the section headings used herein are for organizational purposes only and are not to be construed as limiting the subject matter described.

Methods:

Visual Inspection

Storage stability and agitation samples were analyzed for particles in a light box against both a white and black background. Pictures were taken to document any particles/precipitate formed in these samples.

A350

Absorbance at 350 nm was monitored to track formation of large, soluble aggregates in storage stability and agitation samples. For these measurements, 300 µL of solution was measured in a reduced volume, 1 cm path-length quartz cuvette. MQ water was used as the blank for all measurements. Note, A350 is a light scattering technique, so it is most effective for measuring scattering in solutions containing large, soluble aggregates, or solutions with a homogeneous dispersion of non-soluble particles.

Example 1

Carbetocin was obtained as a powder and was stored at ≤20° C. until ready for use. Formulations were prepared by dissolving 40 mg/mL or 20 mg/mL of carbetocin in an aqueous solution containing a solubilizer and/or HPMC. The pH of each formulation was adjusted to 5.4 and ±0.1 by addition of an appropriate amount of 5 M NaOH. All preparations were prepared using multi-compendial grade excipients and reagents, and ultra-pure water (Millipore MilliQ, 18MΩ). The osmolality of each preparation was measured before preparing the final formulation to ensure it was similar to that of the theoretically determined value. Each formulation (bulk material) was sterile filtered using a Millipore Millex-GV syringe filter (0.22 µm). 1.2 mL of each sterile filtered formulation was filled into a 3 mL glass vial, stoppered with a 13 mm Fluorotec coated serum stopper, and crimped. All materials (i.e., vials, stoppers, etc.) were sterilized before filling. For samples with reduced or limited headspace, a 1 mL vial was used instead of a 3 mL vial. After sterile preparation, samples were placed horizontally on an orbital plate shaker (Labnet, 3 mm orbit) and shaken continuously at 200 rpm for a prescribed period of time (see Table 1). Samples were shielded from ambient light during agitation. All samples used in this study were agitated at room temperature. The results of this experiment are summarized below in Table 1.

TABLE 1

Visual Observation Results of Agitated Carbetocin Formulations

| Solubilizer | Carbetocin (mg/mL) | HPMC % (w/v) | Headspace | Orientation | Observations |
|---|---|---|---|---|---|
| 50 mM Arg HCl | 40 | 0.05 | Limited | Horizontal | 1 piece of soft precipitate after 4 days |
| 200 mM Arg HCl | 40 | None | 30% | Horizontal | No precipitation after 5 hrs of agitation, but significant precipitation after 24 hrs |
| 200 mM Arg HCl | 40 | 0.05 | 30% | Horizontal | Some particles at 2 days; with a few large, "soft precipitate" particles |
| 400 mM Proline | 40 | None | 30% | Horizontal | Significant precipitation after 1 day |
| 100 mM Nicotinamide | 40 | None | 30% | Horizontal | Significant precipitation after 1 day |
| 300 mM Nicotinamide | 40 | None | 30% | Horizontal | Some very fine particles after 2 days, but not obvious; same appearance at 4 days |
| 300 mM Nicotinamide | 40 | 0.05 | 30% | Horizontal | Some particles at 1 day; with a few large, "soft precipitate" particles |
| 300 mM Nicotinamide | 40 | 0.005 | 30% | Horizontal | Some particles at 1 day; with a few large, "soft precipitate" particles |
| 300 mM Nicotinamide | 20 | None | 30% | Horizontal | Perhaps a few fine particles after 3 days, but not obvious |

The results presented in Table 1 show that these high carbetocin concentration preparations (i.e., 40 mg/mL, 20 mg/mL) in pure water (pH 5.4) with various excipients show visual signs of precipitation, but differences in the precipitation behavior were observed dependent on the excipient and excipient concentration. Under the selected conditions (see Table 1 above), it can be seen that both arginine and proline were not effective at suppressing particle formation in the concentration ranges examined. In contrast, 300 mM nicotinamide significantly helped to suppress particle formation when used as the sole formulation excipient. Additionally, nicotinamide was more effective at suppressing particle formation when the concentration of carbetocin in the formulation was reduced from 40 mg/mL to 20 mg/mL. However, under the tested conditions, nicotinamide was not effective at suppressing particle formation when its concentration was reduced to 100 mM.

It was also observed that the morphology of the particles formed in 300 mM nicotinamide solutions were different than those seen in the other carbetocin formulations studied. The particles generated in agitated nicotinamide formulations were granular/fine in nature, and their formation did not seem to progress substantially with prolonged agitation of the solution.

The results show that nicotinamide alone, or in combination with hydroxypropyl methylcellulose (HPMC), was effective at mitigating precipitation of carbetocin upon prolonged agitation. While particles/precipitate may form with both of these excipients, the amounts formed are significantly less than that of the other excipients studied.

Example 2

Samples were prepared using the general procedure provided in Example 1. It is noted that the hydrotropes studied in this example were formulated at the following concentrations: 160 mM (isotonic) and 400 mM sodium benzoate, 200 mM (isotonic) and 400 mM sodium salicylate, and 82 mM caffeine (near solubility limit), and 35 mg/mL carbetocin. Again, as in Example 1, an agitation study was conducted to evaluate the ability of these solutions to suppress particle formation upon agitation. Observations were made after both 14 and 24 hours of agitation.

After 14 hours, the following was observed: the benzoate preparations/samples (160 mM and 400 mM) formed a hard precipitate. The caffeine preparation formed a carbetocin skin on the vial wall. The salicylate preparations formed a few fine particles, but were otherwise generally clear. After 24 hrs of agitation, the 200 mM salicylate preparation had slightly more particles/precipitate than its 400 mM counterpart. Additionally, the 200 mM salicylate preparation had a slight opalescent appearance.

Figure 2:
FIG. 2. shows an example image of various samples studied after 6 days of continuous agitation. From left to right: 400 mM sodium salicylate, 200 mM sodium salicylate, 82 mM caffeine, and 160 mM sodium benzoate after 6 days of continuous agitation.

It was further observed that the caffeine preparation had a similar appearance to the 400 mM salicylate preparation. As a result, the sample agitation was continued. After five days of additional agitation, the samples were once again observed for particle formation. Both salicylate preparations were minimally changed from their earlier (i.e., their 24 hr appearance) (see FIG. 1), while the caffeine sample had formed a hard precipitate. An image comparing the salicylate, caffeine, and benzoate samples after 6 days of agitation is shown in FIG. 2.

The result of this agitation study showed that salicylate may behave similarly to nicotinamide in suppressing particle formation with agitation. It is noted that nicotinamide can be utilized at much higher concentrations (i.e., 400 mM is isotonic) than salicylate (200 mM is isotonic), due to its tonicity properties.

Example 3

Formulations were prepared according to the method described in Example 1 by dissolving the desired amount of 40 mg/mL of carbetocin in an aqueous solution containing different excipients or HPMC. The pH of each formulation was adjusted to 5.4 and ±0.1 by addition of an appropriate amount of 5 M NaOH. After sterile preparation according to the same method described in Example 1, samples were placed horizontally on an orbital plate shaker (Labnet, 3 mm orbit) and shaken continuously at 200 rpm for prescribed periods of time. Samples were shielded from ambient light during agitation. All samples used in this study were agitated at room temperature. The results of this experiment are summarized below in Tables 2 and 3.

TABLE 2

Visual Observation Results for Agitated Carbetocin Formulations

| Carbetocin Concentration | Excipient | Vial Orientation | Agitation Time (hrs) | Observations |
|---|---|---|---|---|
| 40 mg/mL DS | Hydroxypropyl β-Cyclodextrin | Horizontal | 17 | Significant precipitation |
| 40 mg/mL DS | 1% (w/v) Hydroxypropyl cellulose | Horizontal | 17 | Gelled |
| 40 mg/mL DS | 0.1% (w/v) Hydroxypropyl methyl cellulose (HPMC) | Horizontal | 17 | Only a few particles ("soft precipitate") and some gel pieces on the glass |
| 40 mg/mL DS | 0.02% (w/v) Poloxamer 188 | Horizontal | 17 | Significant precipitation |
| 40 mg/mL DS | 0.1% (w/v) Poloxamer 188 | Horizontal | 17 | Significant precipitation |

As can be seen from Table 2, poloxamer 188 (a nonionic block co-polymer surfactant) and hydroxypropyl-β-cyclodextrin, both of which have been shown to be effective at suppressing interfacial damage of proteins in solution, failed to stabilize carbetocin. Precipitation of carbetocin occurred within 17 hours of agitation when formulated with both of these excipients. In addition, hydroxypropyl cellulose (HPC) caused the solution to gel after 17 hrs of agitation. Conversely, HPMC appeared to be relatively effective at mitigating precipitation, with only a few pieces of larger, "soft" precipitate being present in the vial after 17 hrs of agitation.

TABLE 3

| Carbetocin (mg/mL) | HPMC, % (w/v) | Potassium Sorbate, % (w/v) | Vial Position | Fill Volume | Shake Time | Observations |
|---|---|---|---|---|---|---|
| 40 | 0.05 | 0.5 | Horizontal | 30% | 24 hrs | Some "soft" precipitate |
| 40 | 0.01 | 0.5 | Horizontal | 30% | 24 hrs | Some "soft" precipitate |
| 40 | 0.005 | 0.5 | Horizontal | 30% | 24 hrs | Some "soft" precipitate |
| 40 | 0.05 | None | Horizontal | 30% | 24 hrs | Some "soft" precipitate |
| 40 | 0.01 | None | Horizontal | 30% | 24 hrs | Some "soft" precipitate |
| 40 | 0.005 | None | Horizontal | 30% | 24 hrs | Some "soft" precipitate |
| 40 | 0.05 | 0.5 | Horizontal | 67% | 24 hrs | Some "soft" precipitate |
| 40 | 0.01 | 0.5 | Horizontal | 67% | 24 hrs | Some "soft" precipitate |
| 40 | 0.005 | 0.5 | Horizontal | 67% | 24 hrs | Some "soft" precipitate |

Inspection of the agitation results in Table 3 shows that all formulations formed soft precipitate within 24 hours of agitation. The amount of precipitate was essentially the same for all concentrations of HPMC investigated, with each formulation containing a few pieces of "soft" precipitate at 24 hrs. Additionally, it appeared as if the amount of precipitate was slightly less for the samples with reduced headspace (67% fill volume). The presence of the preservative potassium sorbate did not appear to negatively impact particle formation. Continued agitation of these samples (up to a week) resulted in only a slow increase in the amount of soft precipitate present.

It was also found that 0.005% (w/v) HPMC is the practical lower limit of this excipient in terms of providing a protective benefit during agitation. Concentrations of 0.001% (w/v) HPMC were shown to be less effective than 0.005% in suppressing particle formation.

Example 4

For this study, carbetocin was formulated at 15, 25, and 35 mg/mL in an aqueous solution of 400 mM nicotinamide at a pH of 5.4±0.1 according to the method described in Example 1. A350 measurements and visual observations were made over a time-course of 14 days. Samples were agitated (horizontal orientation) at both 5° C. and 25° C., and measurements were taken at time-zero, 3 days, and 14 days. A corresponding set of controls (no agitation) were measured at the conclusion of the study. The results of the A350 measurements at time-zero, 3 days, and 14 days are listed below in Table 4, while visual observations are given in Table 5. Graphical depictions of the A350 values for samples with and without headspace are given in FIG. 3(a) and FIG. 3(b), respectively.

TABLE 4

A350 values measured for samples stored at 5° C. and 25° C. for zero (t = 0), 3 days (d), and 14 days (d)

| Sample | Headspace | t0 | 14 d Ctrl | 3 d 5° C. | 3 d 25° C. | 14 d 5° C. | 14 d 25° C. |
|---|---|---|---|---|---|---|---|
| 15 mg/mL | 80% | 0.011 | 0.010 | 0.014 | 0.014 | 0.022 | 0.025 |
| 25 mg/mL | 80% | 0.017 | 0.017 | 0.018 | 0.025 | 0.058 | 0.042 |
| 35 mg/mL | 80% | 0.023 | 0.023 | 0.026 | 0.046 | 0.037 | 0.081 |
| 15 mg/mL | Limited | 0.011 | 0.014 | N.M. | 0.019 | 0.016 | 0.013 |
| 25 mg/mL | Limited | 0.017 | 0.019 | N.M. | 0.022 | 0.030 | 0.024 |
| 35 mg/mL | Limited | 0.023 | 0.030 | N.M. | 0.031 | 0.049 | 0.037 |

N.M. = not measured

TABLE 5

Visual inspection results of samples stored at 5° C. and 25° C. for zero (t = 0), 3 days (d), and 14 days (d)

| Sample | Head Space | t0 | 14 d Ctrl | 3 d 5° C. | 3 d 25° C. | 14 d 5° C. | 14 d 25° C. |
|---|---|---|---|---|---|---|---|
| 15 mg/mL | 80% | x | x | x | x | precipitate | precipitate |
| 25 mg/mL | 80% | x | x | x | x | precipitate | precipitate |
| 35 mg/mL | 80% | x | x | x | x | precipitate | precipitate |
| 15 mg/mL | Limited | x | x | x | x | x | x |
| 25 mg/mL | Limited | x | x | x | x | precipitate | x |
| 35 mg/mL | Limited | x | x | x | x | precipitate | precipitate | x = no evidence of visible particles/precipitate in these samples

Figure 3A:
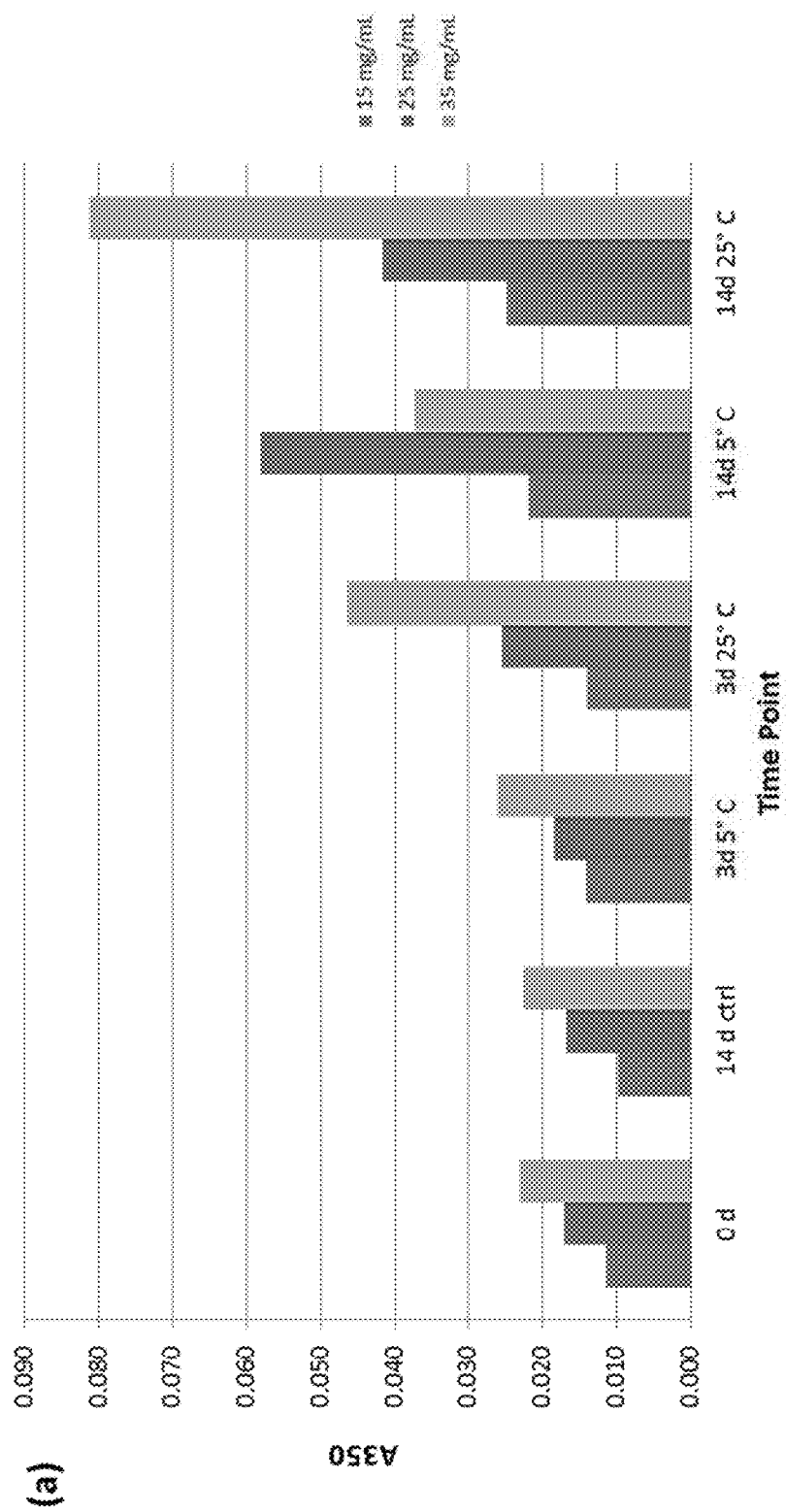
FIG. 3. shows A350 measurements for various samples.
Figure 3B:
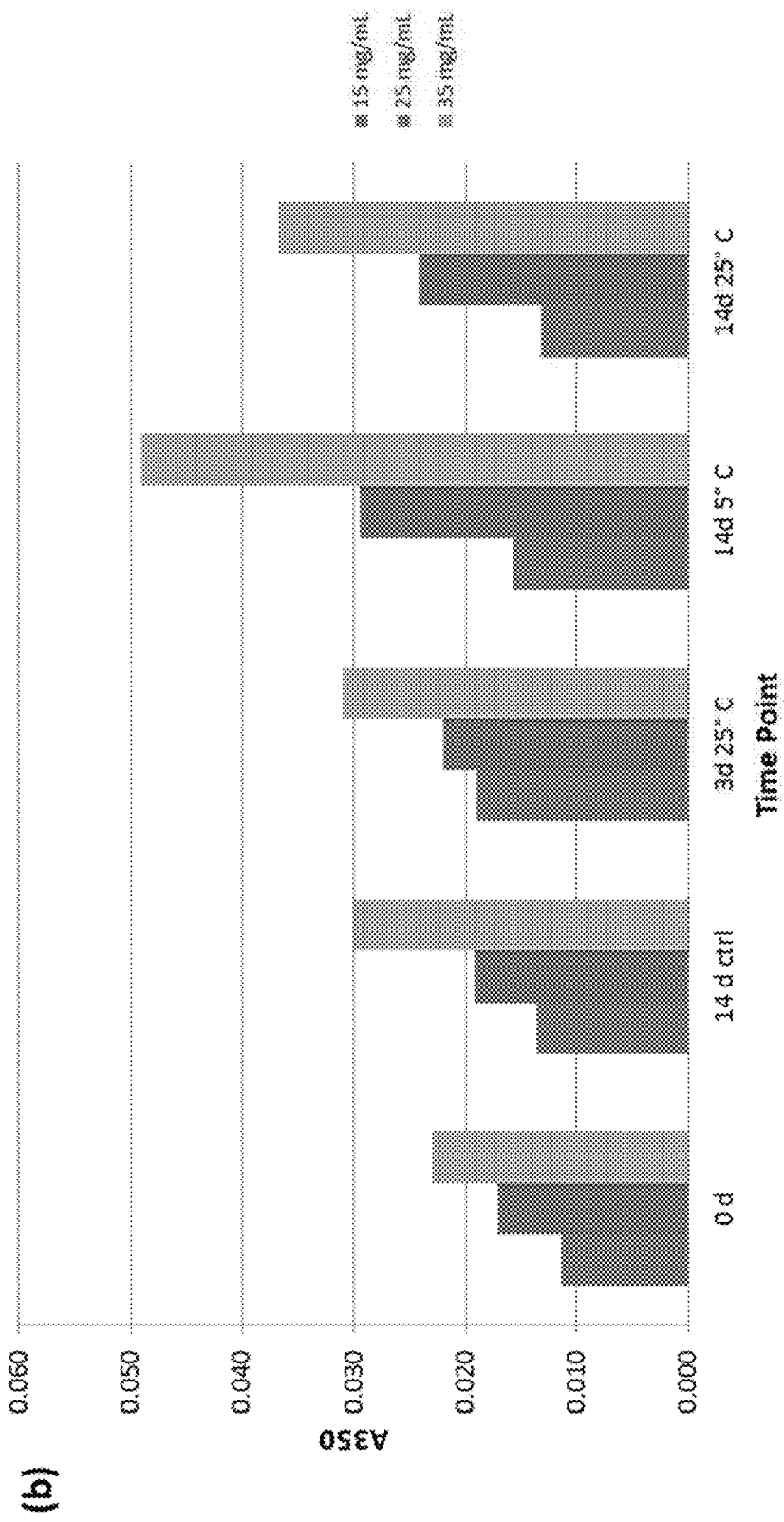

The A350 data in Table 4, as well as FIGS. 3(a) & 3(b), shows that A350 values tend to increase with increasing carbetocin concentration. Additionally, for the headspace samples, the propensity to form aggregates/precipitate has both a concentration and temperature dependence, with the 25° C., 35 mg/mL sample showing the largest increase in A350 versus time-zero. The effect of limiting the headspace to near zero appears to have a measurable benefit from the A350 measurements, although multiple samples at both the 5° C. and 25° C. agitation condition had visible particles/precipitate after 14 days of agitation. After 5 days of continuous agitation, no visible signs of precipitate were seen for the preparations studied; as a result, the final time-point was extended to 14 days. Only after 7 days of agitation were visible particles/precipitate evident in these samples.

The effects of carbetocin loading/concentration, temperature, and vial headspace on the precipitation behavior of carbetocin were studied. From this study it was found that the propensity to precipitate was concentration dependent, with higher concentration samples precipitating more readily than lower concentration samples. Additionally, for samples containing headspace, it appeared as if the propensity to precipitate increased with increasing temperature. Limiting vial headspace may decrease the amount of aggregates/precipitate formed during agitation.

Example 5

Formulations were prepared according to the method described in Example 1. The carbetocin concentration for all formulations was 35 mg/mL, and the pH was adjusted to 5.4±0.1. The formulations investigated in Example 5 are listed below in Table 6.

TABLE 6

Example 5 formulation design

| Form | ZnCl$_2$ (mM) | Citrate (mM) | Acetate (mM) | Sorbitol (mM) | Arg HCl (mM) | Nicotinamide (mM) | EDTA (% w/v) | Sorbate (% w/v) | HPMC (% w/v) | Me-β-Cy (mM) |
|---|---|---|---|---|---|---|---|---|---|---|
| 1 | 0 | 0 | 10 | 225 | 0 | 0 | 0.1 | 0.12 | 0 | 0 |
| 2 | 35 | 35 | 7.4 | 0 | 0 | 0 | 0 | 0 | 0 | 0 |
| 3 | 25 | 0 | 25 | 0 | 0 | 0 | 0 | 0.12 | 0 | 0 |
| 4 | 25 | 12.5 | 7.4 | 0 | 0 | 0 | 0 | 0 | 0 | 17.5 |
| 5 | 0 | 0 | 7.4 | 0 | 0 | 200 | 0.1 | 0.12 | 0 | 0 |
| 6 | 0 | 0 | 7.4 | 227 | 0 | 0 | 0 | 0 | 0 | 0 |
| 7 | 0 | 0 | 7.4 | 0 | 50 | 200 | 0.1 | 0.12 | 0 | 0 |
| 8 | 0 | 0 | 7.4 | 200 | 0 | 0 | 0 | 0 | 0 | 35 |
| 9 | 35 | 17.5 | 7.4 | 0 | 0 | 200 | 0 | 0 | 0 | 0 |
| 10 | 0 | 0 | 7.4 | 0 | 0 | 0 | 0.1 | 0.12 | 0.05 | 0 |
| 11 | 0 | 0 | 50 | 200 | 0 | 0 | 0 | 0 | 0.05 | 0 |
| 12 | 0 | 0 | 7.4 | 0 | 0 | 200 | 0 | 0 | 0.01 | 0 |
| 13 | 0 | 0 | 7.4 | 0 | 0 | 0 | 0.1 | 0.12 | 0 | 35 |
| 14 | 0 | 0 | 25 | 0 | 0 | 0 | 0 | 0 | 0 | 35 |
| 15 | 0 | 0 | 7.4 | 0 | 50 | 200 | 0 | 0 | 0.01 | 0 |
| 16 | 0 | 0 | 7.4 | 0 | 0 | 300 | 0.1 | 0.12 | 0 | 0 |

TABLE 6-continued

Example 5 formulation design

| Form | ZnCl$_2$ (mM) | Citrate (mM) | Acetate (mM) | Sorbitol (mM) | Arg HCl (mM) | Nicotinamide (mM) | EDTA (% w/v) | Sorbate (% w/v) | HPMC (% w/v) | Me-β-Cy (mM) |
|---|---|---|---|---|---|---|---|---|---|---|
| 17 | 0 | 0 | 7.4 | 200 | 50 | 0 | 0 | 0 | 0 | 0 |
| 18 | 0 | 0 | 7.4 | 270 | 25 | 0 | 0 | 0 | 0 | 17.5 |

Me-β-Cy = methyl-β-cyclodextrin;
sorbate = potassium sorbate

Freeze/Thaw (F/T) Agitation Study

A F/T agitation study was conducted with the formulations listed in Table 6. For this study, two different headspace configurations were tested (12% and 70%). For this study, samples were frozen for ≥24 hrs at −20° C. before thawing. After thawing, samples were allowed to equilibrate to room temperature and then gently swirled to mix (freeze concentration was evident) before starting agitation. Samples were agitated in a horizontal orientation and monitored for particle/precipitate formation at 5 and 19 hrs. Visual observation results from this agitation study are given below in Table 7.

TABLE 7

Appearance of freeze thaw samples after 5 and 19 hrs. of agitation

| Form | 70% Headspace, 5 hrs. | 12% Headspace, 5 hrs. | 70% Headspace, 19 hrs. | 12% Headspace, 19 hrs. |
|---|---|---|---|---|
| 1 | Precipitation | Precipitation | Significant precipitation | Significant precipitation |
| 2 | Fine precipitate on vial wall | Precipitation | Significant precipitation | Significant precipitation |
| 3 | None | Precipitation | Significant precipitation | Significant precipitation |
| 4 | Fine precipitate on vial wall | Fine precipitate on vial wall and some fine particles | Fine precipitate on vial wall | Fine precipitate on vial wall and some fine particles |
| 5 | Maybe a few particles, not definitive | Fine precipitate | Fine precipitate | Fine precipitate |
| 6 | Precipitation | Precipitation | Significant precipitation | Significant precipitation |
| 7 | Maybe a few particles, not definitive | None | Small amount of fine and soft precipitate | Fine precipitate |
| 8 | Maybe a few particles, not definitive | Fine precipitate | Some soft precipitate | Fine precipitate |
| 9 | None | None | Fine precipitate | Fine precipitate on vial wall some fine particles |
| 10 | Some soft precipitate | Some soft and fine precipitate | Some soft precipitate | Some soft and fine precipitate |
| 11 | None | None | Some soft precipitate | Some soft and fine precipitate |
| 12 | None | None | Some soft precipitate | Some soft precipitate |
| 13 | Maybe a few particles, not definitive | Fine precipitate | Some soft precipitate | Fine precipitate |
| 14 | Maybe a few particles, not definitive | Maybe a few particles, not definitive | Some fine precipitate | Some fine and soft precipitate |
| 15 | None | None | Some soft precipitate | Soft precipitate |
| 16 | Fine precipitate | Maybe some fine particles, not definitive | Fine precipitate on vial wall and some fine particles | Fine precipitate |
| 17 | Fine precipitate on vial wall and some particles | None | Significant precipitate | Significant precipitate |
| 18 | Fine precipitate on vial wall and some fine particles | Some fine precipitate | Significant precipitate | Fine precipitate on vial wall and fine precipitate |

As can be seen from Table 7, the majority of samples/preparations demonstrated precipitation after only 5 hours of agitation. Furthermore, there was no noticeable difference in the precipitation behavior of the two different headspace samples. Non-frozen control samples (stored at 5° C.) demonstrated the same type of precipitation behavior as the frozen samples.

It was found that the samples containing HPMC, nicotinamide, and methyl-β-cyclodextrin were less prone to precipitation than samples that did not contain these excipients. The precipitation behavior of samples formulated with methyl-β-cyclodextrin and nicotinamide appeared to be similar, with both types of samples forming fine/granular precipitate upon prolonged agitation. Additionally, these solutions (methyl-β-cyclodextrin and nicotinamide) had an opalescent tinge after 19 hrs of agitation. The presence of opalescence suggests that these solutions may contain larger, soluble aggregates which are yet to precipitate. The results of this study show that the effectiveness of nicotinamide at suppressing particle formation was concentration dependent, with 300 mM being more effective than 200 mM. Additional agitation studies conducted with nicotinamide demonstrated that 400 mM>350~300 mM>200 mM at suppressing particle formation. The visual rank ordering for the samples highlighted in gray in Table 7 is as follows: (F11, F12)≥(F10, F14, F15)>(F5, F8, F13, F16)>(F7, F9). This rank ordering is based on visual observations.

The best performing formulations from the F/T agitation study were used as solubilizers to reconstitute pure, lyophilized carbetocin at 35 mg/mL. Reconstitution times of lyophilized carbetocin using these solubilizers are listed in Table 8.

TABLE 8

Reconstitution time of lyophilized carbetocin using the formulation samples in Table 7

| Solubilizer/Blank (no solubilizer) | Solubilizer | Recon Time |
| --- | --- | --- |
| F5 | 200 mM Nicotinamide | 2 min 20 s |
| F7 | 50 mM Arg/200 mM Nicotinamide | 1 min 50 s |
| F8 | 35 mM Me-β-CD | 4 min 30 s |
| F9 | 200 mM Nicotinamide | 4 min |
| F11 | None | >30 min |
| F12 | 200 mM Nicotinamide | 5 min |
| F13 | 35 mM Me-β-CD | 1 min 30 s |
| F14 | 35 mM Me-β-CD | 2 min 20 s |
| F15 | 50 mM Arg/200 mM Nicotinamide | 2 min |
| F16 | 300 mM Nicotinamide | 1 min |

Recon = reconstitution;
Me-β-CD = Methyl-β-Cyclodextrin

As can be observed from Table 8, all samples containing a solubilizer had reconstitution times of 5 minutes or less. But samples without a solubilizer (i.e., F11) had very long reconstitution times (i.e., >30 min).

Following reconstitution, these samples were subjected to an identical agitation study as described previously for the F/T samples. The visual observation results from this agitation study are given below in Table 9.

TABLE 9

Appearance of reconstituted lyo samples after 2, 5, and 19 hrs of agitation

| Solubilizer/Blank (no solubilizer) | Precipitate at 2 hrs | Precipitate at 5 hrs | Precipitate at 19 hrs |
| --- | --- | --- | --- |
| F5 | No | No | Yes |
| F7 | No | No | Yes |
| F8 | No | No | Yes |
| F9 | No | No | Yes |
| F11 | No | Maybe | Yes |
| F12 | No | No | Yes |
| F13 | No | No | Yes |
| F14 | No | No | Yes |
| F15 | No | No | Yes |
| F16 | No | Maybe | Yes |

A visual rank ordering of the reconstituted lyo samples after 19 hours of agitation was as follows: F15>(F13, F14)≥(F12, F8)≥(F11, 400 mM nicotinamide>(F05, F07, F09, F16, 350 mM nicotinamide). This rank was made using visual observations.

Figure 4:
FIG. 4. shows an example image of "soft" precipitate for 2 HPMC containing samples on the left vs. "hard" or significant precipitate for the two HPMC samples on the right.
Figure 5:
FIG. 5. shows an example image of "fine" precipitate, as found in 350 and 400 mM nicotinamide samples (19 hrs agitation).

It was found that formulations containing HPMC, methyl-β-cyclodextrin, and nicotinamide were the most resistant to precipitation upon agitation, but do eventually form some precipitate. The morphologies of the precipitate formed with these excipients are different, with HPMC forming a few, large "soft" particles (see FIG. 4) while nicotinamide and methyl-β-cyclodextrin form smaller, more granular particles. Concentration ranging experiments for nicotinamide indicated that the effectiveness of this solubilizer at suppressing precipitation increases with increasing nicotinamide concentration (see FIG. 5).

Example 6

Additional reconstitution examples are provided in Table 10. Arginine, as well as hydrotropes like proline and nicotinamide, were selected to improve the dissolution times. In addition, the effect of solids content on dissolution rate was examined. The results of these reconstitution studies are given in Table 10.

TABLE 10

Reconstitution time of pure carbetocin lyophilisate with various excipients and at various reconstitution volumes

| Excipient | Lyo Sample | Recon. Volume | Final Recon. Conc. (mg/mL) | Recon. Time |
| --- | --- | --- | --- | --- |
| 25 mM Arg HCl | 40 mg/mL carbetocin | Full | 40 | 18 min |
| 50 mM Arg HCl | 40 mg/mL carbetocin | Full | 40 | 8 min |
| 50 mM Arg/Glu | 40 mg/mL carbetocin | Full | 40 | 16 min |
| 100 mM Arg HCl | 40 mg/mL carbetocin | Full | 40 | 3 min |
| 200 mM Arg HCl | 40 mg/mL carbetocin | Full | 40 | 1 min, 50 s |
| 200 mM Lysine HCl | 40 mg/mL carbetocin | Full | 40 | >10 min |
| 400 mM Proline | 40 mg/mL carbetocin | Full | 40 | 5 hrs |
| 300 mM Nicotinamide | 40 mg/mL carbetocin | Full | 40 | 1 min, 30 s |
| 100 mM Nicotinamide | 40 mg/mL carbetocin | Full | 40 | 5 min, 50 s |

TABLE 10-continued

Reconstitution time of pure carbetocin lyophilisate with various excipients and at various reconstitution volumes

| Excipient | Lyo Sample | Recon. Volume | Final Recon. Conc. (mg/mL) | Recon. Time |
|---|---|---|---|---|
| 0.5% Potassium Sorbate | 40 mg/mL carbetocin | Full | 40 | >25 min |
| Water | 40 mg/mL carbetocin | ½ | 20 | 30 min |
| Water | 5 mg/mL carbetocin | ¼ | 20 | 3 min |
| Water | 10 mg/mL carbetocin | ¼ | 40 | 5 min, 30 s |
| 50 mM Arg HCl | 10 mg/mL carbetocin | ¼ | 40 | 4 min |
| 200 mM Arg HCl | 10 mg/mL carbetocin | ¼ | 40 | 2 min, 20 s |

Recon. = reconstitution;
Conc. = carbetocin concentration

Conditions which expedited the dissolution of pure carbetocin lyo material (re-lyophilized carbetocin, cake form) are provided in Table 10. It was found that 200 mM arginine and 300 mM nicotinamide both dramatically improved the dissolution rate of lyophilized carbetocin. Utilizing these solubilizers, dissolution times of the re-lyophilized carbetocin (at 40 mg/mL) were reduced to only a few minutes. The solubilizing power of these particular excipients was concentration dependent, with increasing concentrations of the excipient decreasing dissolution time. Proline was not effective as a solubilizer at the concentration (400 mM) examined in this study.

The results further indicate (see Table 10) that while potassium sorbate did not expedite dissolution of lyophilized carbetocin, it did not negatively impact dissolution either.

Regarding the effect of solids content on dissolution rate, it was found that a reduced volume for reconstitution of carbetocin lyophilized at a lower solids content yielded faster dissolution rates than carbetocin lyophilized at a higher solids content (see Table 10). It was further found that the dissolution rates for the lower solids content material were similar to those of the solubilizers (like nicotinamide or arginine), although they were not superior.

It was found that isotonic solutions of arginine and nicotinamide could efficiently solubilize carbetocin lyophilisate, and thus could potentially be utilized as a solubilizer for lyophilized carbetocin.

Example 7

Exemplary Stable Pharmaceutical Preparations of Carbetocin

Exemplary pharmaceutical preparations of carbetocin are provided in Tables 11-13.

TABLE 11

Pharmaceutical Preparations of Carbetocin

| Form | pH | Carbetocin (mg/ml) | Acetate (mM) | Sodium Benzoate (mM) | Sorbitol (mM) | HPMC (%, w/v) | Nicotinamide (mM) | K + Sorbate (%, w/v) | EDTA (%, w/v) |
|---|---|---|---|---|---|---|---|---|---|
| 1 | 5.4 | 1 | 5 | 0 | 0 | 0 | 400 | 0 | 0 |
| 2 | 5.4 | 1 | 5 | 0 | 110 | 0.01 | 200 | 0 | 0 |
| 3 | 5.4 | 1 | 5 | 160 | 0 | 0 | 0 | 0 | 0 |
| 4 | 5.4 | 1 | 5 | 0 | 287 | 0.01 | 0 | 0 | 0 |
| 5 | 5.4 | 1 | 5 | 0 | 287 | 0.05 | 0 | 0 | 0 |
| 6 | 5.4 | 1 | 5 | 0 | 0 | 0.05 | 400 | 0 | 0 |

*HPMC = hydroxypropyl methylcellulose;
$K^+$ = potassium;
EDTA = ethylenediaminetetraacetic acid

TABLE 12

Pharmaceutical Preparations of Carbetocin

| Form | pH | Carbetocin (mg/ml) | NaCl (mM) | Sorbitol (mM) | Nicotinamide (mM) | Acetate (mM) | HPMC (%, w/v) |
|---|---|---|---|---|---|---|---|
| 1 | 5.4 | 34.3 | 0 | 250 | 0 | 0 | 0 |
| 2 | 5.4 | 34.3 | 0 | 250 | 0 | 0 | 0.05 |
| 3 | 5.4 | 34.3 | 0 | 110 | 200 | 0 | 0.01 |
| 4 | 5.4 | 34.3 | 0 | 0 | 400 | 0 | 0 |
| 5 | 5.4 | 25 | 0 | 110 | 200 | 1.6 | 0.01 |

*HPMC = hydroxypropyl methylcellulose

TABLE 13

| | | | | K + | | |
|---|---|---|---|---|---|---|
| Form | pH | Carbetocin (mg/ml) | EDTA (%, w/v) | Sorbate (%, w/v) | HPMC (wt %, w/v) | Nicotinamide (mM) |
| 1 | 5.4 | 34.3 | 0 | 0 | 0.01 | 400 |
| 2 | 5.4 | 34.3 | 0.1 | 0.12 | 0.01 | 400 |
| 3 | 5.4 | 34.3 | 0 | 0 | 0 | 0 |

*HPMC = hydroxypropyl methylcellulose;
K⁺ = potassium;
EDTA = ethylenediaminetetraacetic acid

What is claimed is:

1. A method of treating Präder-Willi syndrome comprising administering intranasally to a subject having Präder-Willi syndrome three doses per day of 3.2 mg/dose carbetocin, for at least one month, wherein the administration results in a decrease in hyperphagia compared to placebo.

2. The method of claim 1, wherein the dose is administered before a meal.

3. The method of claim 2, wherein each dose is administered within 30 minutes of a meal.

4. The method of claim 1, wherein the carbetocin is administered for at least two months.

5. The method of claim 2, wherein the carbetocin is administered for at least two months.

6. The method of claim 1, wherein the administration of carbetocin further results in one or more of: (a) decrease in obsessive and compulsive behavior compared to placebo; (b) decrease in anxiety compared to placebo; or (c) improvement in global clinical impression compared to placebo.

7. The method of claim 2, wherein the administration of carbetocin further results in one or more of: (a) decrease in obsessive and compulsive behavior compared to placebo; (b) decrease in anxiety compared to placebo; or (c) improvement in global clinical impression compared to placebo.

8. The method of claim 2, wherein the administration of carbetocin results in a decrease in anxiety.

9. The method of claim 2, wherein the administration of carbetocin results in a decrease in obsessive and compulsive behavior.

10. The method of claim 1, wherein the administration of carbetocin results in a decrease in hyperphagia behavior and a decrease in obsessive and compulsive behavior.

11. The method of claim 1, wherein the administration of carbetocin results in a decrease in anxiety.

12. The method of claim 1, wherein the subject has an age ranging from seven (7) to eighteen (18) years old, inclusive.

13. The method of claim 1, wherein the subject is aged seven (7) years old.

14. The method of claim 1, wherein the administration of carbetocin results in a decrease in measurement of Hyperphagia Questionnaire for Clinical Trials (HQ-CT) Total Score.

15. The method of claim 1, wherein the administration of carbetocin results in a decrease in measurement of the PWS Anxiety and Distress Questionnaire (PADQ) Total Score.

16. The method of claim 1 wherein the carbetocin is administered in an aqueous solution comprising:
    (a) carbetocin or a pharmaceutically acceptable salt thereof, wherein the carbetocin is present in a concentration of about 10 mg/mL to about 70 mg/mL; and
    (b) a hydrotrope, and wherein the solution has little to no visible solids.

17. The method of claim 16, wherein the pharmaceutical preparation has little to no visible solids after shaking for 1, 2, or 3 days at 5° C. and/or 25° C.

18. The method of claim 16, wherein the hydrotrope is nicotinamide.

19. The method of claim 1 wherein the carbetocin is administered in an aqueous solution comprising:
    (a) carbetocin or a pharmaceutically acceptable salt thereof, wherein the carbetocin is present in a concentration of about 10 mg/mL to about 70 mg/mL;
    (b) nicotinamide;
    (c) HPMC; and
    (d) one or more additional excipients.

* * * * *